(12) United States Patent
Hillmyer et al.

(10) Patent No.: US 10,160,741 B2
(45) Date of Patent: Dec. 25, 2018

(54) RECOVERY OF MONOMER FROM POLYURETHANE MATERIALS BY DEPOLYMERIZATION

(71) Applicant: REGENTS OF THE UNIVERSITY OF MINNESOTA, Minneapolis, MN (US)

(72) Inventors: Marc Andrew Hillmyer, Minneapolis, MN (US); Tessie Rose Panthani, Minneapolis, MN (US); Marie Elizabeth Vanderlaan, Minneapolis, MN (US); Deborah Kay Schneiderman, Minneapolis, MN (US); Alexander Michael Rauch Mannion, Minneapolis, MN (US); Derek Charles Batiste, Minneapolis, MN (US); Christopher Ward Macosko, Minneapolis, MN (US); Jay Z. Wang, Kildeer, IL (US); Frank S. Bates, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/728,878

(22) Filed: Oct. 10, 2017

(65) Prior Publication Data
US 2018/0030023 A1 Feb. 1, 2018

Related U.S. Application Data

(62) Division of application No. 15/442,829, filed on Feb. 27, 2017, now Pat. No. 9,815,808.

(60) Provisional application No. 62/301,126, filed on Feb. 29, 2016.

(51) Int. Cl.
*C07D 309/30* (2006.01)
*C08G 81/02* (2006.01)

(52) U.S. Cl.
CPC ......... *C07D 309/30* (2013.01); *C08G 81/027* (2013.01)

(58) Field of Classification Search
CPC .................................................. C07D 309/30
USPC ....................................................... 549/273
See application file for complete search history.

(56) References Cited

U.S. PATENT DOCUMENTS

| | | |
|---|---|---|
| 4,451,583 A | 5/1984 | Chesler |
| 4,609,680 A | 9/1986 | Fujita |
| 5,342,969 A | 8/1994 | Ford |
| 5,414,113 A | 5/1995 | Broeker |
| 5,502,247 A | 3/1996 | Bartos |
| 5,559,159 A | 9/1996 | Sublett |
| 5,668,186 A | 9/1997 | Brunelle |
| 6,136,869 A | 10/2000 | Ekart |
| 6,472,557 B1 | 10/2002 | Pell |
| 6,916,939 B2 | 7/2005 | Yamane |
| 8,758,828 B2 | 6/2014 | Markland |
| 9,815,808 B2 * | 11/2017 | Hillmyer .............. C08G 81/027 |
| 2008/0039540 A1 | 2/2008 | Reitz |

FOREIGN PATENT DOCUMENTS

| | | | |
|---|---|---|---|
| EP | 0865464 B1 | 5/2001 | |
| JP | 2009241417 A | 9/1997 | |
| JP | 2006-299179 A | 11/2006 | |
| JP | 2008-201679 A | 9/2008 | |
| JP | 2014185117 | * 10/2014 | ........... C07D 310/12 |
| WO | WO 1995002625 A2 | 1/1995 | |
| WO | WO 2014172596 A2 | 10/2014 | |
| WO | WO 2015161169 A1 | 10/2015 | |

OTHER PUBLICATIONS

Szymanski, Macromol. Theory Simul. 7,27-39 (1998).*
Martello, Dissertation, University of Minnesota, Apr. 2014.*
Abe, "Degradation Processes of End-Capped Poly(L-Lactide)s in the Presence and Absence of Residual Zinc Catalyst" May 2004 *Biomacromolecules* 5:1606-1614.
ACS Abstract, "Sustainable and Recyclable Polyurethanes" Abstract ID: 2393962, 251st American Chemical Society National Meeting & Exposition, San Diego CA, Mar. 13-17, 2016.
Alam, "Vegetable oil based eco-friendly coating materials: A review article" 2014 *Arabian Journal of Chemistry* 7:469-479.
American Chemistry Council, Economic and Statistics Department, "The Economic Benefits of the U.S. Polyurethanes Industry" 2015.
Anastas, "Green Chemistry: Principles and Practice" Nov. 2009 *Chem. Soc. Rev.*, 39:301-312.
Babb, "Polyurethanes from Renewable Resources" in *Synthetic Biodegradable Polymers* Springer Editor: Rieger (Berlin), 2014, 315-360.
Bagdi, "Specific interactions, structure, and properties in segmented polyurethane elastomers" Nov. 2010 *exPRESS Polymer Letters* 5(2011):417-427.
Bandekar, "FTIR spectroscopic studies of polyurethanes Part 1. Bonding between urethane C—O—C groups and the NH groups" Dec. 1991 *Journal of Molecular Structure* 263(1-2):45-57.
"BASF Science Competition—Lightweight Solutions for a Sustainable Future," Proposal, Nov. 2015.
Bechtold, "Perfectly Alternating Copolymers of Lactic Acid and Ethylene Oxide as a Plasticizing Agent for Polylactide Macromolecules" Nov. 2001 *Macromolecules* 34(25):8641-8648.
Behrendt, "The Chemical Recycling of Polyurethanes" Feb. 2009 *Journal of the University of Chemical Technology and Metallurgy* 44(1):3-23.

(Continued)

*Primary Examiner* — Nizal S Chandrakumar
(74) *Attorney, Agent, or Firm* — Mueting, Raasch & Gebhardt, PA

(57) ABSTRACT

Methods for recovering monomers from polymers, such as polyurethanes (including thermoset polyurethanes) include heating the polymer to depolymerize the polymer and release the monomer. The monomer may be directly recovered. The polymer may include a poly(β-methyl-δ-valerolactone) (PMVL) block and the monomer recovered may be β-methyl-δ-valerolactone (MVL).

7 Claims, 10 Drawing Sheets

(56) References Cited

OTHER PUBLICATIONS

Beltran, "Preparation of Oleochemical Polyols Derived From Soybean Oil" 2011 *Latin American Applied Research* 41:69-74.
Borda, "Gylcolysis of polyurethane foams and elastomers" May 2000 *Polymer Degradation and Stability* 68(3):419-422.
Campbell, "Polyurethane Foam Recycling. Superheated Steam Hydrolysis" 1976 *Environmental Science Technology* 10(2)182-185.
Cinelli, "Green synthesis of flexible polyurethane foams from liquefied lignin" Jun 2013 *European Polymer Journal* 49(6): 1174-1184.
"CSP researchers earn challenge grand prize for work on recyclable foams," Dec. 8, 2015. Online: http://www1.chem.umn.edu/news/news.lasso?serial=1023.
"CSP students among 2015 Dow Sustainability Award finalists," Nov. 19, 2015. Online: http://www1.chem.umn.edu/news/news.lasso?serial=1014.
"CSP team wins BASF Science Competition" Jun. 5, 2015. Online: http://www1.chem.umn.edu/news/news.lasso?serial=908.
Darby, "Fungal Susceptibility of Polyurethanes" Jun. 1968 *Appl. Microbiol.* 16(6):900-905.
De Espinosa, "Plant oils: The perfect renewable resource for polymer science?!" May 2011 *European Polymer Journal*, 47(5):837-852.
Delebecq, "On the Versatility of Urethane/Urea Bonds: Reversibility, Blocked Isocyanate and Non-isocyanate Polyurethane" Jan. 2013 *Chemical Reviews* 113(1):60-118.
Diesendruck, "Mechanically triggered heterolytic unzipping of a low-ceiling-temperature polymer" Mar. 2014 *Nature Chemistry* 6(7):623-628.
Dijkstra, "Chapter 16 Controlled Synthesis of Biodegradable Poly(ester)s" in *Biorelated Polymers: Sustainable Polymer Science and Technology* Chiellini (Ed.) Springer Science: New York; 2001. Cover page, publisher's page, and pp. 179-194.
"Dow SISCA Proposal: Sustainable and Recyclable Polyurethane Foams," Presentation, Nov. 2015.
"Dow Elevator Pitch: Sustainable and Recyclable Foams," BASF Summer Course, Ludwigshafen, Germany, Jul. 2015.
Drobny, *Handbook of Thermoplastic Elastomers, 2nd Edition*. Drobny (Ed.) William Andrew Pub.: Norwich, NY, 2014. Cover page, publisher's page, and pp. 398-404.
Drumright, "Polylactic acid technology" Dec. 2000 *Adv. Mater.* 12:1841-1846.
Duda, "Thermodynamics of L-Lactide Polymerization" Mar. 1990 *Equilibrium Monomer Concentration Macromolecules* 23(6): 1636-1639.
Dupret, "Biodegradation of poly(ester-urethane)s by a pure strain of micro-organisms" Oct. 1999 *Macromol. Chem. Phys.* 200(11):2508-2518.
Dusek, "Network Formation of Polyurethanes Due to Side reactions" Mar. 1990 *Macromolecules* 23 (6): 1774-1781.
Fan, "Rigid Polyurethane Foams made from High Viscosity Soy-Polyols" Feb. 2013 *Journal of Applied Polymer Science* 127(3):1623-1629.
Gurusamy-Thangavelu, "Polyurethanes based on renewable polyols from bioderived lactones" Aug. 2012 *Polym. Chem.* 3:2941.
Heintz, "A Spectroscopic Analysis of the Phase Evolution in Polyurethane Foams" 2005 *Macromolecules* 38(22):9192-9199.
Helling, "Use of life cycle assessment to characterize the environmental impacts of polyol production options" 2009 *Green Chemistry* 11:380-389.
Hermann, "Current policies affecting the market penetration of biomaterials" Nov. 2011 *Biofuels, Bioprod. Bioref.* 5(6):708-719.
Hojabri, "Fatty Acid-Derived Diisocyante and Biobased Polyurethane Produced from Vegetable Oil: Synthesis, Polymerization, and Characterization" Apr. 2009 *Biomacromolecules* 10(4):884-891.
Hong, "Completely recyclable biopolymers with linear and cyclic topologies via ring-opening polymerization of γ-butyrolactone" Nov. 2015 Nature Chemistry 8:42-49.
Howard, "Biodegradation of polyurethane: a review" 2002 *International Biodeterioration and Biodegradation* 49:245-252.
Jamshidi, "Thermal Characterization of polylactides" Dec. 1988 *Polymer* 29(12):2229-2234.
Lebedev, "Thermodynamics of the Polymerization of Lactones" May 1982 *Dokl. Phys. Chem.* 264(1/2/3):334-336.
Lee, "Thermal Decomposition Behavior of Blocked Diisocyanates Derived from Mixture of Blocking Agents" Oct. 2005 *Macromolecular Research* 13(5):427-434.
Li, *Bio-based polyols and polyurethanes*, Springer: Cham, Switzerland, 2015. Cover page, title page and table of contents.
Lligadas, "Plant Oils as Platform Chemicals for Polyurethane Synthesis: Current State of the Art" Oct. 2010 *Biomacromolecules* 11(11):2825-2835.
Liow, "Enhancing mechanical properties of thermoplastic polyurethane elastomers with 1,4-trimethylene carbonate, epsilon-caprolactone, and L-lactide copolymers via soft segment crystallization" 2011 *eXPRESS Polymer Letters* 5(10):897-910.
Lochee, "Biodegradable Poly(ester-ether)s: ring-opening polymerization of D,L-3-methyl-1,4-dioxan-2-ones using various initiator systems" Jun. 2010 *Polym. Int.* 59:1310-1318.
Longley, "β-Methyl-δ-Valerolactone" 1963 *Organic Synthesis Coll.* 4:677.
MacDonald, "An aromatic/aliphatic polyester prepared via ring-opening polymerisation and its remarkably selective and cyclable depolymerisation to monomer" Nov. 2015 *Polymer Chemistry* 7:553.559.
Mahoney, "Hydrolysis of Polyurethane Foam Waste" 1974 *Environmental Science Technology* 8(2): 135-139.
Mannion, "Sustainable and Recyclable Polyurethane Foams" Poster, DOW SISCA Competition, Dec. 13, 2015.
Martello, "Bulk Ring-Opening Transesterification Polymerization of the Renewable δ-Decalactone Using an Organocatalyst" 2012 *ACS Macro Lett.* 1:131-135.
McDonough, Peer Reviewed: Applying the Principles of Green Engineering to Cradle-to-Cradle Design Dec. 2003 *Environmental Science & Technology* 37(23)434A-441A.
McNeil, "Degradation Studies of Some Polyesters and Polycarbonates-2. Polylactide: Degredation Under Isothermal Conditions, Thermal Degradation Mechanism and photolysis of the Polymer" 1985 *Polymer Degradation and Stability* 11(4):309-326.
Molero, "Recovery of polyols from flexible polyurethane foam by 'split-phase' glycolysis with new catalysts" 2006 *Polymer Degradation and Stability* 91(2006):894-901.
Nakajima-Kambe, "Microbial degradation of polyurethane, polyester polyurethanes, and polyether polyurethanes" Feb. 1999 *Appl. Microbiol. Bioechnol.* 51(2):134-140.
Neitzel, "Divergent Mechanistic Avenues to an Aliphatic Polyesteracetal or Polyester from a Single Cyclic Esteracetal" Oct. 2014 *ACS Macro Lett.* 3:1156-1160.
Nishida, "Equilibrium Polymerization Behavior of 1,4-Dioxan-2-one in Bulk Macromolecules" Sep. 2000 *Macromolecules* 33(9):6982-6986.
"Our Vision to Transform the Polyurethane Industry," Dow SISCA Competition Presentation, Dec. 2015.
"Our Vision to Transform the Polyurethane Industry," BASF 150th Anniversary North American Science Competition, Jun. 2015.
Palaskar, "Synthesis of Biobased Polyurethane from Oleic and Ricinoleic Acids as the Renewable Resources via the AB-Type Self-Condensation Approach" May 2010 *Biomacromolecules* 11(5): 1202-1211.
Pawlik, "Influence of Palm Oil-Based Polyol on the Properties of Flexible Polyurethane Foams" Jun. 2012 *J. Polym. Environ* 20(2):438-445.
Persenaire, "Mechanisms and Kinetics of Thermal Degredation of Poly(ε-Caprolactone)" Feb. 2001 *Biomacromolecules* 2(1):288-294.
Petrovic, "Vegetable oil-based triols from hydrofomylated fatty acids and polyurethane elastomers" Jan. 2010 *Eur. J. Lipid Sci. Technol.* 112(1):97-102.
Petrovic, "Polyester Polyols and Polyurethanes from Ricinoleic Acid" Apr. 2008 *Journal of Applied Polymer Science* 108(2): 1184-1190.

(56) References Cited

OTHER PUBLICATIONS

Petrovic, "Polyurethanes from Vegetable Oils" Feb. 2008 *Polymer Reviews* 48(1):109-155.
"Project to develop recyclable polyurethane foam wins $10K Dow SISCA prize," Dec. 9, 2015. Online: https://twin-cities.umn.edu/news-events/project-develop-recyclable-polyurethane-foam-wins-10k-dow-sisca-prize.
Saralegi, "Thermoplastic polyurethanes from renewable resources: effect of soft segment chemical structure and molecular weight on morphology and final properties" Jan. 2013 *Polymer International* 62(1)106-115.
Save, "Controlled Ring—Opening Polymerization of Lactones and Lactides Initiated by Lanthanum Isopropoxide, 1 General Aspects and Kinetics" 2002 *Macromol. Chem. Phys.* 203(5/6):888-889.
Schneiderman, "Chemically Recyclable Biobased Polyurethanes" Apr. 2016 *ACS Macro Lett.* 5:515-518.
Schneiderman, "Aliphatic polyester block Polymer Design" Mar. 2016 *Macromol.* 49:2419-2428.
Simon, "Novel polyol initiator from polyurethane recycling residue" 2014 *J. Mater. Cycles Waste Manag.* 16:525-532.
Simon, "Sustainable Polyurethanes: Chemical Recycling to Get It" in *Environment and Climate Change l.: Environmental Chemistry of Pollutants and Wastes, Handbook Env Chem.*, vol. 32 Jimenez (Ed.), Springer: Berlin; 2015. Cover page, publisher's page, and pp. 229-260.
Sobczak, "Synthesis and Characterization of Polyurethane Based on Oligo(ε-caprolactone) Prepared by Free-Metal Method" May 2011 *Journal of Macromolecular Science, Part A: Pure and Applied Chemistry* 48:373-380.
Sonnenschein, "Enhancing polyurethane properties via soft segment crystallization" Nov. 2005 *Polymer* 46(23):10158-10166.
Sonnenschein, *Polyurethanes: Science, Technology, Markets and Trends*, John Wiley & Sons Inc.: Hoboken NJ; 2015. Cover page, title page and table of contents.
Tan, "Rigid polyurethane foams from a soybean oil-based Polyol" Jun. 2011 *Polymer*, 52(13):2840-2846.
Tanaka, "Quantitative Study on Hydrogen Bonding between Urethane Compound and Ethers by Infrared Spectroscopy" Aug. 1968 *Journal of Polymer Science A-1* 6(8):2137-2152.
Tang, "Thermoplastic polyurethane elastomers from biobased poly(δ-decalactone) diols" 2014 *Polym. Chem.* 5(9):3231-3237.
Turner, "The Influence of Viscosity on Cell Opening of a Flexible Molded Foam" 1989 *Journal of Cellular Plastics* 25 (2): 117-124.
University of Minnesota, "Press release: project to develop recyclable polyurethane foam wins 10k Dow SISCA Prize" Dec. 9, 2015. Online: https://www.cems.umn.edu/news/graduate-students-win-10k-dow-sisca-prize.
Versteegen, "Properties and Morphology of Segmented Copoly(ether urea)s with Uniform Hard Segments" 2006 *Macromolecules* 39(2):772-783.
Woods, *The ICI Polyurethanes Book 2$^{nd}$ Ed.* Wiley: New York; 1990. Cover page, title page and table of contents.
Xiong, "The production of mechanically tunable block polymers from sugar" Jun. 2014 *PNAS* 23(111):8357-8362.
Xu, "Morphology and properties of thermoplastic polyurethanes with dangling chains in ricinoleate-based soft segments" 2008 *Polymer* 49:4248-4258.
Yanagishita, "Chemoenzymatic Synthesis and Chemical Recycling of Sustainable Polyurethanes" 2008 *ChemSusChem* 1(1):133-142.
Yang, "Recycling and disposal methods for polyurethane foam wastes" 2012 *Procedia Environmental Sciences* 16:167-175.
Yang, "Thermal degradation of urethanes based on 4,4'-diphenylmethane diisocyanate and 1,4-butane diol (MDI/BDO)" 1986 *Polymer* 27(8):1235-1241.
Yeganeh, "Synthesis and properties of isocyanate curable millable polyurethane elastomers based on castor oil as a renewable resource polyol" Jun. 2004 *European Polymer Journal* 40(6):1233-1238.
Yevstropov, "Calorimetric study of δ-Valerolactone, poly-δ-valerolactone and of the process of polymerization of δ-valerolactone in the 13.8 to 340 K temperature range Vysokomolekuliarnye soedineniia" Jan. 1983 *Seriia A* 24(3):568-574.
Yevstroprov, "The thermodynamic properties of β-propiolactone, its polymer, and its polymerization in the 0-400 K range" Jul. 1980 *Polym. Sci. USSR*, 21(9):2249-2256.
Yilgör, "Critical parameters in designing segmented polyurethanes and their effect on morphology and properties: A comprehensive review" 2015 *Polymer* 58:A1-A36.
Zhang, "Bio-based Polyurethane Foam Made from Compatible Blends of Vegetable-Oil-Based Polyol and Petroleum-based Polyol" Mar. 2015 *Sustainable Chemistry and Engineering* 3(4):743-749.
Zhang, "Bio-Based Polyurethanes Prepared from Different Vegetable Oils" Dec. 2014 *ACS Applied Materials and Interfaces* 7(2):1226-1233.
Zhang, "Catalytic Polymerization of a Cyclic Ester Derived from a 'Cool' Natural Precursor" Jul./Aug. 2005 *Biomacromolecules* 6(4):2091-2095.
Zhang, "Substituting soybean oil-based polyol into polyurethane flexible foams" 2007 *Polymer* 48:6656-6667.
Zlatanic, "Effect of Structure on Properties of Polyols and Polyurethanes Based on Different Vegetable Oils" Jan. 2004 *Journal of Polymer Science Part B: Polymer Physics* 42(5):809-819.

\* cited by examiner

RECOVERY OF MONOMER FROM POLYURETHANE MATERIALS BY DEPOLYMERIZATION

RELATED APPLICATION

This application is a divisional patent application of U.S. patent application Ser. No. 15/442,829, filed on Feb. 27, 2017, which claims the benefit of U.S. Provisional Patent Application No. 62/301,126, filed on Feb. 29, 2016, each of which is hereby incorporated herein by reference in its entirety.

STATEMENT OF GOVERNMENTAL SUPPORT

This invention was made with government support under grant number CHE-1413862, awarded by the National Science Foundation. The government has certain rights in the invention.

FIELD

This disclosure generally relates to, among other things, polymers and recovering monomers from polymers.

INTRODUCTION

Many polymers are derived from petroleum; however in recent years, changing consumer preferences, and government policies, have increased the demand for bio-derived alternatives. For example, a majority of polyurethanes (PUs) on the market today are derived from petrochemicals, but renewable polyols derived from low cost plant oils have attracted considerable attention. Natural oil polyols (NOPs) typically are used in conjunction with petrochemical polyethers, such as ethylene oxide-terminated poly(propylene oxide), when used in flexible foam formulations. Due to the synthetic limitations inherent to most NOPs (i.e., lower end group reactivity and marginal control over functionality and total molar mass) this required or desired blending limits the total bio-based content of the PU. Synthetic strategies have been developed to address some of these limitations. However, these additional modifications increase the cost and the additional processing steps are undesirable from green chemistry and engineering perspectives. Furthermore, the heterogeneous composition of NOPs can lead to inconsistent quality and properties of the final PU product. Additionally, renewable polyurethanes derived from NOPs present similar disposal challenges as traditional, petroleum-derived polyurethanes.

Many polymer materials are resistant to degradation and present environmental challenges associated with large-scale production and disposal of these materials. For example, some PU products such as thermoplastic polyurethanes (TPUs) can be thermally reprocessed, but the cross-linked chemical structure of thermoset polyurethane resins (including foams) prevents melt processing. While not widely used on an industrial scale, research related to the chemical recycling of polyurethanes has been performed. One researched method of chemical recycling, glycolysis, uses the reaction of a glycol with a polyurethane at elevated temperatures to recover polyols suitable for use in the manufacture of new polyurethane materials. A similar chemical recycling method, hydrolysis, uses water to the same effect. The efficacy of these methods is somewhat limited since they naturally produce a mixture of recycled polyols if the foams to be recycled are chemically heterogeneous (i.e., prepared from different polyols). Moreover, the potential side byproducts can be somewhat complex as urethane, urea, biuret, and allophanate groups may all be present in polyurethanes. One disadvantage of these chemical recycling methods is the limited purity of the recovered polyol.

SUMMARY

Described herein, among other things, are methods for recovering monomers from polymers, such as polyurethanes; including, in some embodiments, thermoset polyurethanes. Various embodiments of the methods described herein may remove concerns regarding polyol heterogeneity in recycling processes because the monomer may be directly recovered from the polyurethane, bypassing recovery of the polyol.

Various embodiments described herein provide for recovery of high purity monomer in large quantities. In some embodiments, 50% or more, such as 75% or more, 90% or more, or 95% or more of monomer is released during the methods described herein and may be recovered. In some embodiments, the monomer may be recovered at a purity of 90% or greater, such as 95% or greater.

Because the monomer may, in some embodiments, be directly recovered in high yield and high purity, the monomer may then be polymerized with controlled functionality and molar mass, which may then be used in other applications, such as manufacturing of new polyurethane foams and elastomers. Accordingly, various embodiments of methods described herein, embody a cyclic lifecycle with little waste.

Various embodiments of methods for releasing β-methyl-δ-valerolactone (MVL) from a polymer comprising poly(β-methyl-δ-valerolactone) (PMVL) are described herein. The methods include heating the polymer to cause depolymerization and release of MVL. The polymer may be a polyurethane, such as a thermoplastic or thermoset polyurethane. The polymer may be a foam. In some embodiments, the polymer comprises a PMVL block having a number average molar mass ($M_n$) of 0.25 kg/mol or greater. The heating may be in the presence or absence of a polymerization catalyst, such as a ring opening transesterification catalyst. The polymerization catalyst may be, for example, an organometallic catalyst, such as tin(II) octoate. The temperature at which the polymer is heated and the time of the heating may vary depending on, among other things, whether a polymerization catalyst is employed. In some embodiments, the polymer is heated at a temperature of 150° C. or greater, such as in a range from 150° C. to 300° C. or in a range from 180° C. to 240° C.

The method may further comprise recovering the released MVL, for example, via distillation. In various embodiments, 50% or more, such as 75% or more, 90% or more, or 95% or more, of the released MVL may be recovered. In some embodiments, the release MVL may be recovered at a purity of 90% or greater, such as 95% or greater. The recovered MVL may be petroleum-based or bio-based. If the recovered MVL is bio-based, the MVL may have a $^{14}C/^{12}C$ ratio greater than zero.

Various embodiments of methods for releasing a lactone monomer from a polymer comprising polyester derived from lactone monomer are described herein. The lactone has a bulk ceiling temperature of 600° C. or less. The method includes heating the polymer to cause depolymerization and release of lactone monomer. The polymer may be a polyurethane, such as a thermoplastic or thermoset polyurethane. The polymer may be a foam. The monomer may be any suitable lactone monomer, such as an alkyl-substituted δ-lactone and ε-caprolactone or a γ-lactone monomer. For example, the lactone monomer may be δ-decalactone, α-methyl-δ-valerolactone, or γ-methyl-δ-valerolactone. The polyester preferably has a glass transition temperature of 20° C. or less. The heating may be in the presence or absence of a polymerization catalyst, such as a ring opening transesterification catalyst. The polymerization catalyst may be an organometallic catalyst, such as tin(II) octoate. The temperature at which the polymer is heated and the time of the heating may vary depending on, among other things, whether a polymerization catalyst is employed. In some embodiments, the polymer is heated at a temperature of 150° C. or greater, such as in a range from 150° C. to 300° C. or in a range from 180° C. to 240° C. The method may further comprise recovering the released lactone monomer, for example, via distillation.

Various embodiments of methods for releasing a monomer from a polymer comprising homopolymer block are described herein. The homopolymer block has a bulk ceiling temperature of 600° C. or less. The method includes heating the polymer to cause depolymerization and release of the monomer. The homopolymer block preferably has a glass transition temperature of 20° C. or less. The polymer may be a polyurethane, such as a thermoplastic or thermoset polyurethane. The polymer may be a foam. The heating may be in the presence or absence of a polymerization catalyst. The method may further comprise recovering the monomer, for example, via distillation.

In some embodiments, a thermoset polyurethane foam is described herein. The polyurethane foam comprises a poly (β-methyl-δ-valerolactone) block. The poly(β-methyl-δ-valerolactone) block may be polymerized from bio-based MVL monomers.

BRIEF DESCRIPTION OF THE DRAWINGS

FIG. 7A: Foam M2700-A; FIG. 7B: Foam M2700-B; FIG. 7C: Foam M2700-C; FIG. 7D: Foam M2700/5200-D; FIG. 7E: Foam M2700-E; FIG. 7F commercial foam (MCM00017).

Figure 1:
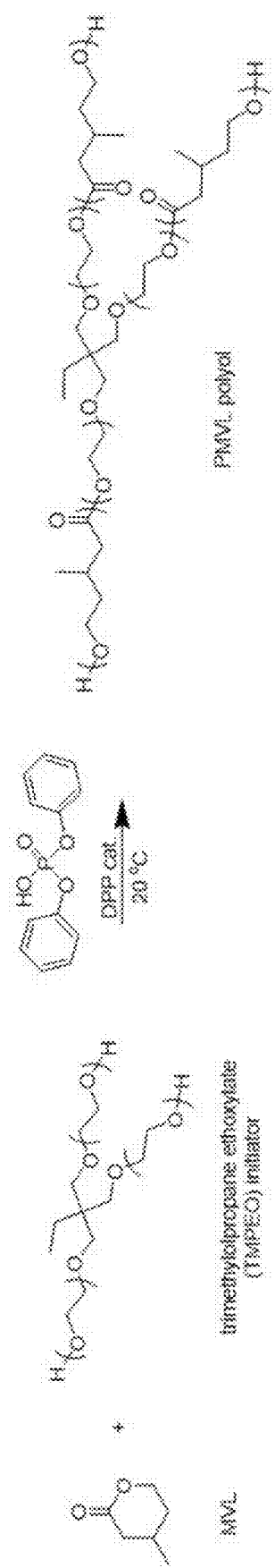
FIG. 1 is a schematic illustration of an embodiment of a synthetic scheme for polymerizing bio-derived MVL monomer into PMVL bio-derived polyol at room temperature with no solvent. In the illustrated embodiment, a low molar mass trifunctional alcohol, TMPEO, is added to control the polyol molar mass and functionality.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, and methods are disclosed. It is to be understood that other embodiments are contemplated and may be made without departing from the scope or spirit of the present disclosure. The following detailed description, therefore, is not to be taken in a limiting sense.

This disclosure generally relates to, among other things, polymers and recovering monomers from polymers. In many embodiments, the polymers are polyurethanes, such as thermoplastic or thermoset polyurethanes. The polyurethanes may be foams.

Polyurethanes described herein may be formed in any suitable manner, such as such as by reacting one or more polyol with one or more isocyanate. In some embodiments, the polyol comprises poly(β-methyl-δ-valerolactone) (PMVL), preferably a bio-based PMVL. Recovery of the monomer by depolymerization of the PMVL comprises recovery of the cyclic lactone β-methyl-δ-valerolactone (MVL) monomer from the PMVL.

MVL may be prepared by an efficient semisynthetic route and may be polymerized at room temperature without the use of solvent to obtain PMVL, a rubbery polyester with a low glass transition temperature. As described herein PMVL may be used in the formation of polyurethane (PU) foams and elastomers. PMVL derived PUs show similar mechanical properties to those currently on the market, demonstrating feasibility of the PMVL polyol as an alternative for petroleum-derived polyols. Moreover, the ability to chemically recycle crosslinked foam back to MVL monomer is demonstrated herein. Recycling foam to monomer instead of polyol is a superior strategy, since the recovered monomer may be polymerized into polyols of any desired molecular weight and functionality. The synthesis and depolymerization strategies described herein bypass some of the technical challenges that currently prevent the industrial-scale chemical recycling of polyurethanes.

MVL may be polymerized to form a PMVL polyol in any suitable matter. For example, a PMVL polyol may be formed via ring-opening transesterification polymerization (ROTEP) of MVL employing an appropriate initiator and catalyst. Any suitable catalyst may be employed. Examples of suitable catalysts include metal catalysts or organocatalysts, such as tin octoate; triethyl aluminum; zinc dibutoxide; titanium tetrabutoxide; triazobicyclodecene (TBD); 1,4-benzene dimethanol (BDM); diphenyl phosphonic acid (DPP); hydrochloric acid; and the like. Any suitable initiator may be employed. For example, the initiator may be an organometal (e.g. alkyl lithium, alkyl magnesium bromide, alkyl aluminum, etc.), a metal amide, an alkoxide, a phosphine, an amine, an alcohol, or the like. Preferably, the initiator is an alcohol. The initiator may be monofunctional or multi-functional. Examples of suitable ring opening transesterification polymerization alcohol initiators include benzyl alcohol; 1,4 benzene dimethanol; 3,3'-((1,3-bis(2-hydroxyethoxy)propane-2,2-diyl)bis(oxy))bis(propan-1-ol); butane-1,4-diol; propane-1,3-diol; propane-1,2,3-triol; trimethylolpropane; 2,2'-((2-ethyl-2-((2-hydroxyethoxy)methyl)propane-1,3-diyl)bis(oxy))bis(ethan-1-ol); and the like. One of skill in the art will understand that the ratio of monomer to initiator may be varied to obtain polymers of different molecular weights. One of skill in the art will also understand that forming of a polyurethane from a PMVL polyol that was formed using a tri- or higher functional initiator may result in a cross-linked polyurethane. It is also possible to obtain cross-linked polyurethane using linear polyols with a multifunctional chain extender of or multifunctional isocyanate.

Polymerization of MVL to form a PMVL polyol may occur in solution, in the melt, or as a suspension.

A PMVL polyol may be a homopolymer or a copolymer. In some embodiments, a PMVL polyol comprises a PMVL block and a block of another polymer, preferably a soft block. In some embodiments, the PMVL polyol is a random copolymer. If the PMVL polyol is a copolymer, preferably the copolymer is a low bulk ceiling temperature monomer. For example, suitable PMVL polyols may be formed from PMVL-co-polydecalactone or PMVL-co-polycaprolactone. Preferably, the PMVL polyol comprises a PMVL homopolymer.

The PMVL polyol may be of any suitable length. In some embodiments, a PMVL polyol has a number average molar mass ($M_n$) of 0.25 kg/mol or greater, such as 0.5 kg/mol or greater, or 1 kg/mol or greater. In some embodiments, a PMVL polyol has $M_n$ of from about 0.1 kg/mol to about 100 kg/mol, such as from about 0.2 kg/mol to about 50 kg/mol, from about 0.5 kg/mol to about 20 kg/mol or from about 1 to about 10 kg/mol.

The PMVL polyols may have any suitable properties. For example, the PMVL polyols may have a glass transition temperature (Tg) of less than −30° C., such as less than −40° C., less than −50° C., or less than −60° C. In many embodiments, a PMVL polyol has a Tg greater than −100° C. In some embodiments, the PMVL polyol has a Tg from about −45° C. to about −70° C.

Preferably, the MVL used to form a PMVL polyol is a bio-based MVL. A biosynthesized compound may be distinguished from a similar compound produced by conventional chemical processes from, for example, a petroleum-based material by the ratio of $^{14}C$ to $^{12}C$ in a sample of the compound. A sample of the compound that is biosynthesized will possess a measurable amount of $^{14}C$ isotopes incorporated into the compound molecules. A sample of the compound prepared from petroleum-based materials will possess negligible levels of $^{14}C$. Thus, a sample or composition that includes a biosynthesized compound (e.g., MVL) will typically possess a $^{14}C/^{12}C$ ratio greater than zero. In some cases, a sample or composition that includes a biosynthesized compound may have a $^{14}C/^{12}C$ ratio greater than $0.25 \times 10^{-12}$ such as, for example, a $^{14}C/^{12}C$ ratio from $0.25 \times 10^{-12}$ to $1.2 \times 10^{-12}$.

In some embodiments, the PMVL portion of a polyurethane described herein has a $^{14}C/^{12}C$ ratio greater than zero. In some cases, the PMVL portion may have a $^{14}C/^{12}C$ ratio greater than or equal to $0.25 \times 10^{-12}$ such as, for example, a $^{14}C/^{12}C$ ratio from $0.25 \times 10^{-12}$ to $1.2 \times 10^{-12}$.

In some embodiments, a polyurethane described herein has a $^{14}C/^{12}C$ ratio greater than zero. In some cases, the block copolymer may have a $^{14}C/^{12}C$ ratio greater than $0.25 \times 10^{-12}$ such as, for example, a $^{14}C/^{12}C$ ratio from $0.25 \times 10^{-12}$ to $1.2 \times 10^{-12}$.

While much of this disclosure relates to bio-derived MVL, it will be understood that the teachings presented herein may also apply to non-bio-derived MVL, such as petroleum-derived MVL.

A PU polymer comprising PMVL may be formed via reaction of one or more di- or polyisocyanates with one or more PMVL polyols, and optionally one or more polyols that do not contain PMVL. In some embodiments, the polyurethane is a hard block containing phase-separated and semi-crystalline domains and the PMVL portion is a soft block. Any suitable compound having two or more isocyanate groups and any suitable PMVL polyol may be used to form a PU. Examples of suitable compounds having two or more isocyanate groups include methylene diphenyl diisocyanate (MDI), toluene diisocyanate (TDI), isophorone diisocyanate, L-lysine diisocyanate, and the like. Examples of suitable PMVL polyols include those described above. Examples of suitable optional polyols include 1,3 propane diol, 1,4 butane diol, and other polyols described above, and the like. Cross-linking may occur through the use of multifunctional isocyanates or multi-functional chain extenders.

In various embodiments, the processes described herein are used to form a thermoplastic polyurethane. The thermoplastic polyurethane may be an elastomer that combines a PMVL block with a hard polyurethane thermoplastic block. Such thermoplastic elastomers behave like elastomers at temperatures between the glass transition temperatures of PMVL and the polyurethane polymer of the hard block and may be processed like thermoplastics at temperatures above the glass transition temperature of the polymer of the polyurethane hard block. In block copolymers having a PU hard block and a PMVL block, the PMVL (soft) segments may influence the elastic nature of the block copolymer and may contribute to low temperature properties and extensibility of the block copolymer.

In some embodiments, the processes described herein may be used to form thermoset PUs. In some embodiments, the thermoset PU is a PU foam. A PU foam comprising PMVL may be formed in any suitable manner. For example, with the exception of utilizing a PMVL polyol, the same protocols that are utilized in industry for foam production may be used. Accordingly, a PMVL polyol is a viable alternative for existing petroleum derived polyols. The functionality and molecular weight of the polyol, and ratio of isocyanate to polyol may be altered to tune foam properties from soft and flexible to hard and rigid. The molecular weight and hydroxyl number of the PMVL may be readily controlled, providing the ability to tune the properties of resulting PU foams to meet product demands. Synthetic parameters (e.g. type of surfactant, polyol molecular weight, polyol hydroxyl functionality, and polyol to isocyanate ratio) may be tailored to achieve desired resulting properties.

In some embodiments, PU foams are formed by reacting a PMVL polyol with an isocyanate in the presence of a blowing agent or catalyst, a gelling agent, and optionally a chain extender, auxiliary blowing agents, inorganic fillers, surfactants, etc.

Embodiments of the PU foams described herein may be derived from annually renewable resources and may be recycled at the end-of-life. The MVL monomer may be prepared using a semisynthetic route whereby mevalonate is produced by fermentation followed by a chemical dehydration and hydrogenation. The polymerization reaction of this monomer into polyols may be performed using an organocatalyst in the presence of an alcohol initiator at room temperature and, in some embodiments, may be performed without a solvent. See, for example, FIG. 1.

In the embodiment depicted in FIG. 1, a low molar mass trifunctional alcohol, TMPEO, is added to control the polyol molar mass and functionality. TMPEO is illustrated as one example of an initiator that may be used, and it will be understood that other initiators may also be utilized. By adjusting the ratio of monomer to added alcohol initiator, it is possible to control of the polyol molecular weight. Target weights ranging from ~1000 g/mol to ~100,000 g/mol have been reproducibly synthesized. Additionally, the number of hydroxyl groups of the polyol may be controlled by using different initiators.

Figure 2:
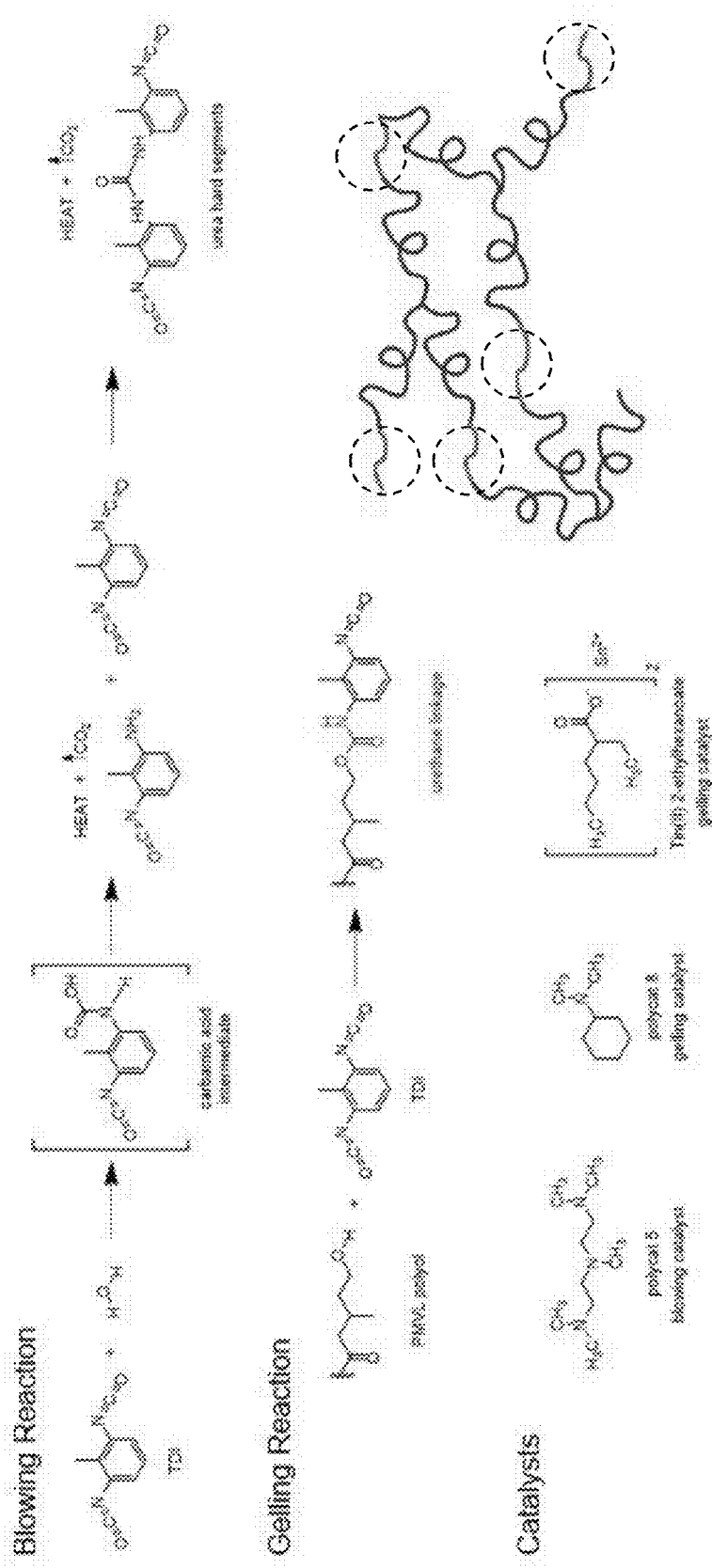
FIG. 2 is a schematic illustration of an embodiment of a synthetic scheme representing blowing and gelling reactions taking place when making a PMVL polyurethane foam. Structures of catalysts used in a representative formulation are also shown. Segments within the dashed circles represent polyurethane segments.

An example of a synthetic scheme for producing a PMVL PU foam is illustrated in FIG. 2. In the embodiment illustrated in FIG. 2, examples of blowing and gelling reactions that may take place when producing a PMVL polyurethane foam are shown. Structures of catalysts used in the illustrated embodiment are shown. It will be understood that the process for producing a PMVL polyurethane foam depicted in FIG. 2 is shown merely for purposes of illustration and not limitation, and that other suitable processes may be employed.

Regardless of how a PMVL-containing PU is formed, the PMVL-containing PU may be recycled as in accordance with the teachings presented herein. In many embodiments, recycling of PMVL-containing PUs is superior to existing methods for recycling existing PUs. Like all PU foams, the PMVL foams described herein are crosslinked thermoset materials that cannot be melted and remolded. However, a chemical recycling process to recover MVL monomer may be employed.

The recycling process comprises heating the PU to cause depolymerization of the PMVL. For example, the PU may be heated at a temperature from about 150° C. to about 300° C.; preferably from about 180° C. to about 240° C. In some embodiments, a polymerization catalyst is added to facilitate depolymerization. If a catalyst is not present, depolymerization may occur at higher temperatures or may take additional time. Preferably, the catalyst is a ring opening transesterification polymerization catalyst, such as those described above. In some embodiments, the ring opening transesterification polymerization catalyst is an organometallic catalyst, such as tin (II) octoate. The catalyst may be present in any suitable amount. For example, the catalyst may be present in an amount from 0.001 weight percent to about 1 weight percent. By way of example, tin (II) octoate in an amount of about 0.3 weight percent has been shown to effectively facilitate depolymerization of PMVL in PU foams at temperatures from about 180° C. to about 240° C. In some instances, a suitable catalyst may already be present in a suitable amount if the catalyst in the PU foam. For example, tin (II) octoate is commonly used as a blowing catalyst in the foam formulation.

The MVL monomer produced as a result of depolymerization of PMVL may be recovered in any suitable manner. For example, a distillation process may be used to continuously remove MVL monomer from the foam as the MVL forms. Using such a method, recovery of 75% of the total theoretical monomer in greater than 95% purity has been demonstrated.

While much of the description presented herein is related to polyurethanes containing PMVL polyols which comprise PMVL blocks, it will be understood that the teachings presented herein may more generally be applied to polymers other than polyurethanes that contain PMVL, or to other low bulk ceiling temperature polymers, particularly low bulk ceiling temperature polymers having low glass transition temperatures that are or may be modified to form polyols for use in polyurethanes.

For example, monomers from polymers having bulk ceiling temperatures of less than 600° C. may be recovered in a manner similar to MVL as described herein. Preferably, the polymers have a bulk ceiling temperature of 350° C. or less. Even more preferably, the polymers have a bulk ceiling temperature of 250° C. or less. Typically, the polymers will have a bulk ceiling temperature of greater than 50° C. For purposes of example, homopolymer PMVL polyols or blocks described herein have a bulk ceiling temperature of about 230° C.

Ceiling temperature is a measure of a tendency of polymers to revert to their monomers. When a polymer is at its ceiling temperature, the rate of polymerization and depolymerization of the polymer are equal. At temperatures above the ceiling temperature the rate of depolymerization is greater than the rate of polymerization. This ceiling temperature is independent of catalyst concentration and structure but depends on polymer and monomer concentration, and the solvent used.

If the polymers (other than PMVL) are to be incorporated into polyurethanes, the polymers preferably form soft blocks. For example, the polymers may have a glass transition temperature of about 20° C. or less, such as about 0° C. or less, about −10° C. or less, or about −20° C. or less. Typically the polymer blocks will have a glass transition temperature of greater than about −100° C.

If the polymers are to be incorporated into polyurethanes, such as polyurethane foams, the polymer blocks are polyols. In some embodiments the polymers are polyesters, which may be formed from ring opening transesterification of lactone monomers in a manner similar to polymerization of MVL to PMVL as described herein. For example, the lactone monomers may be alkyl-substituted ε-lactone, δ-lactone, or γ-lactone monomers. Specific examples of suitable lactone monomers that may be polymerized into polyols via ring opening transesterification using a polyol initiator include δ-decalactone [bulk ceiling temperature of about 150° C.], α-methyl-δ-valerolactone [bulk ceiling temperature of about 560° C.], γ-methyl-δ-valerolactone, [ceiling temperature of about 320° C.], and the like. The polymerization of such monomers or combinations thereof may be performed in a manner similar to the polymerization of the lactone monomer MVL described herein, and the incorporation of the resulting polyol block into polyurethanes may be performed in a manner similar to incorporation of PMVL polyols described herein. The polyols may be formed from copolymerization of two or more of these lactones, and optionally from copolymerization with MVL.

Similarly, the depolymerization or depolymerization and recovery of the monomers may be performed in a manner similar to that described herein regarding PMVL blocks.

In the description above several specific embodiments of compounds, compositions, products and methods are disclosed. It is to be understood that other embodiments are contemplated and may be made without departing from the scope or spirit of the present disclosure. The description, therefore, is not to be taken in a limiting sense.

In the following non-limiting examples that provide illustrative embodiments of the compositions, food products, methods and sweetness enhancers described above. These examples are not intended to provide ay limitation on the scope of the disclosure presented herein.

Examples

Figure 3:
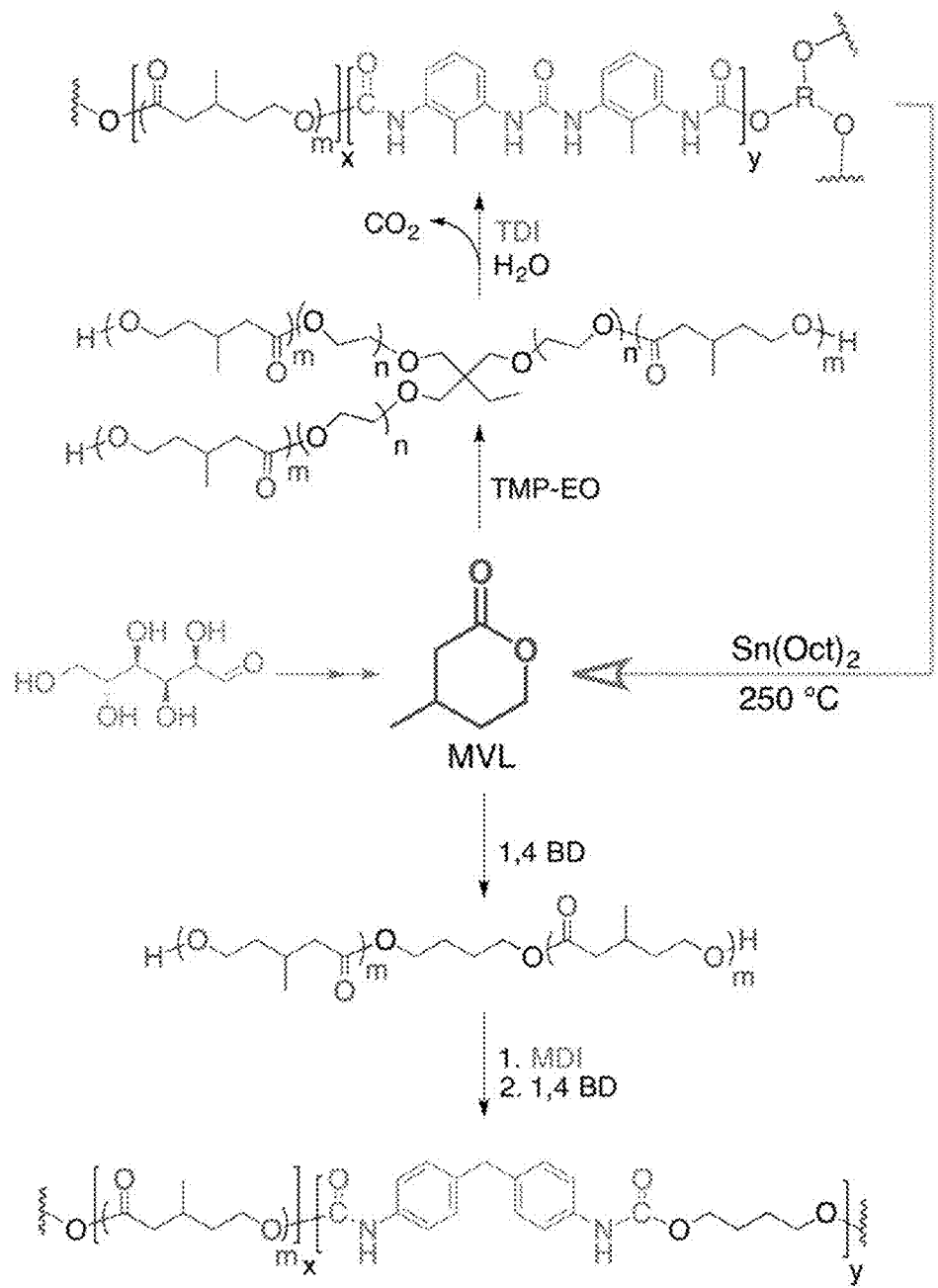
FIG. 3 is a schematic illustration of an embodiment of a synthetic scheme for producing thermoplastic polyurethanes (TPUS) and chemically recyclable foams from MVL.

FIG. 3 illustrates an example of a scheme for synthesis of thermoplastic PUs (TPUs) and chemically recyclable foams from MVL.

In the example shown in FIG. 3, n≈2.5/3 and m=$N_n$/f where $N_n$ and f are the degree of polymerization and functionality of the PMVL polyol, respectively. Both materials may be approximated as segmented block polymers where x and y are the respective weight fractions of the soft and hard segments. Because the polyurethane polymerizations are step-growth reactions, the number of repeating units within the hard segments is not precisely known.

Methods

PMVL Polyol Synthesis:

MVL may be produced in any suitable manner. For example, MVL may be produced from sugar using a semi-synthetic approach but also may be produced in one step via the dehydrogenation of 3-methyl-1,5-pentane diol. MVL may be polymerized in the bulk at room temperature.

An acid (either diphenyl phosphate [DPP] or HCl in diethyl ether) was used to catalyze the polymerization of MVL. Under typical conditions (bulk, 20° C., $[MVL]_0$/[Cat.]≈50, $10<[MVL]_0$/[ROH]<100), the polymerization approached equilibrium within 3 hours. The equilibrium monomer conversion was 91% at 20° C. but increased to 95% at −20° C. The purification procedure depended on the specific catalyst used. If HCl is used as the polymerization catalyst, both it and MVL monomer may be removed in vacuo without quenching. Because HCl is more volatile than the lactone, it may be removed rapidly from the polymer without significant PMVL depolymerization. The diphenyl phosphate catalyzed reactions were quenched by addition of triethylamine (TEA) in chloroform. In each case the resulting polymer solution was washed with cold aqueous sodium hydroxide (0.1 N solution, 0° C.) to remove MVL, DPP, and TEA. Under these conditions the aqueous washes hydrolyze MVL to the corresponding water-soluble hydroxy acid form but do not affect polymer structure.

PMVL TPU Synthesis:

Thermoplastic polyurethanes were prepared from PMVL using a two-step, one-pot procedure. (This general synthetic strategy is commonly used in the synthesis of TPUs from MDI. An isocyanate-terminated prepolymer was first generated in situ by adding a DMF solution of $Sn(Oct)_2$ and hydroxyl terminated PMVL diol to methylene diphenyl diisocyante (MDI) at 70° C. The ratio of PMVL to MDI was adjusted to target different compositions; however, in each case there was a large excess (≥10 functional group equivalents) of isocyanate relative to alcohol. The solution was stirred for 0.5 h after the addition of PMVL to ensure the polymer was fully end capped, then chain extender (either 1,3 propane diol or 1,4 butane diol) was added to prepare the TPU. The amount of chain extender added was adjusted to maintain a slight excess of isocyante (~1.1 eq) relative to total hydroxyl groups. It has previously been demonstrated that this two-step strategy results in higher uniformity of the hard blocks, and consequently enhances thermal and mechanical properties, when compared to TPUs prepared using a one-pot, one-step process. After stirring overnight at 70° C., the reactions were cooled and the TPU samples were isolated by dropwise precipitation in methanol (this precipitation is believed to remove $Sn(Oct)_2$ from the sample). The TPU samples thus obtained were dried in a vacuum oven prior to analysis.

PMVL Foam Synthesis:

The procedure employed for the synthesis of PMVL soft foams mimics the two-component formulations commonly used industrially. First, PMVL polyol, surfactant (Dabco 5164), blowing (Polycat5) and gelling (Polycat8) catalysts, and blowing agent (water) were mixed in a 10 ounce polypropylene cup (in some samples an additional catalyst, stannous octoate [$Sn(Oct)_2$], was also added). Then, toluene diisocyanate (TDI) (a 80:20 mixture of 2,4 and 2,6 isomers) was added and components were homogenized for ~10 seconds. Stirring was then stopped and the foam was allowed to rise freely. In some samples the rise profile was recorded and temperature was monitored using a thermocouple embedded in the center of the cup. Foams were allowed to cure at room temperature for at least 24 hours prior to characterization. The top and bottom of the foams were trimmed off and samples were cut from the center of the core and used for mechanical characterization and density measurements.

Results

Figure 4A:
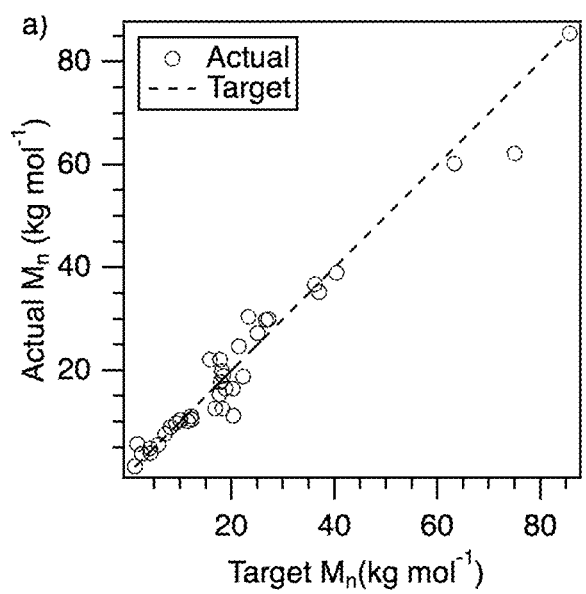
FIG. 4A is a plot showing targeted molar mass ($[M]_0/[I]_0*p$) and observed $M_w$ (by MALLS-SEC) of several linear PMVL polyols (where p is the fractional conversion determined by $^1$H NMR). The molar masses ranged from approximately 1 kg mol$^{-1}$ to nearly 100 kg mol$^{-1}$.
Figure 4B:
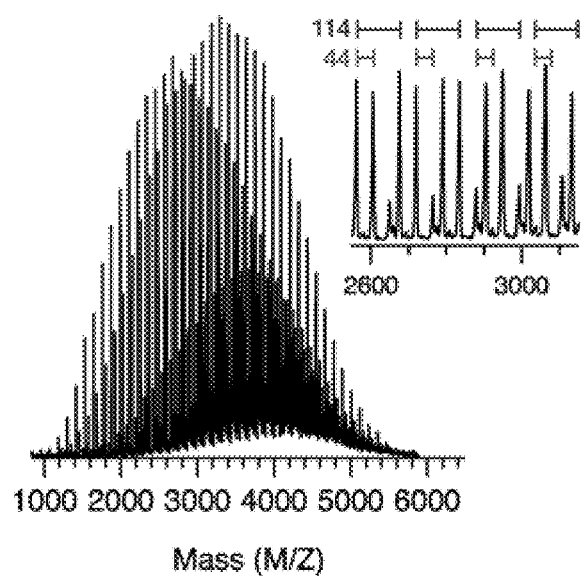
FIG. 4B is a matrix-assisted laser desorption/ionization MALDI plot of PMVL2700 triol used for foam formulations. The PMVL2700 triol was synthesized using trimethylolpropane ethoxylate (with a distribution of EO lengths, nominal average molar mass of ~170 grams mol$^{-1}$) as an initiator. Polymer chains initiated by four different species, specifically trimethylolpropane ethoxylate with 0, 1, 2, and 3 ethylene oxide repeats, are present. As shown in the inset, these different species are separated by the molar mass of ethylene oxide (44.05 grams mol$^{-1}$). For chains with different degrees of polymerization initiated by the same alcohol, the difference in molar mass per repeat unit is the same as the molar mass of MVL monomer (114.15 grams mol$^{-1}$).

As shown in FIG. 4A, by adjusting the ratio of MVL monomer to added alcohol initiator it is possible to access hydroxyl telechelic PMVL polyols with molar masses ranging from approximately 1 kg mol$^{-1}$ to nearly 100 kg mol$^{-1}$. Whereas polyols used for the synthesis of polyurethane elastomers and foams are typically only low to moderate molar mass polymer; higher lower molar mass polymers are valuable for a number of other applications (e.g., the synthesis of block polymer adhesives and elastomers). Practically, the molar mass range is limited on the lower end by initiator solubility and on the upper end by monomer purity. The functionality of the polyol may be controlled by using different alcohol initiators. Whereas trimethylolpropane ethoxylate was used to prepare a trifunctional polyol for use in foam formulations, various diol initiators (e.g. 1,4 butane diol, 1,3 propane diol, and 1,4 benzene dimethanol) were employed to synthesize linear polyols for the synthesis of TPUs. As demonstrated in FIG. 4B, matrix-assisted laser desorption/ionization (MALDI) was used to confirm molar mass control and to verify initiator structures.

The molecular characteristics of the PMVLs used are summarized in Table 1. For all samples there was good agreement between the targeted molar mass, the molar mass estimated by proton nuclear magnetic resonance spectroscopy ($^1$H NMR) end group analysis, and the molar mass determined using MALDI. Moreover, the dispersity ($Đ$) values calculated from the MALDI data were similar to those determined using size exclusion chromatography with a multi-angle light scattering detector (MALLS-SEC). As expected, the glass transition temperature ($T_g$) values of the PMVL polyols, found using differential scanning calorimetry (DSC), were significantly lower than the $T_g$ of high molar mass PMVL (about −60° C. and −50° C., respectively). Similar to other polyester polyols, the zero-shear viscosities (η) of the PMVL diol and triol samples are slightly higher than amorphous polyether polyols of comparable molar mass. The PMVL viscosities are within the range of the polyol viscosities typically used for PU foams.

Characteristics of representative PMVL TPU samples are summarized in Table 2. Using a standard definition of hard segment content, specifically the weight ratio of the sum of the MDI and chain extender to the total mass of the polymer, hard segment contents ranging from 0.3 to 0.6 were targeted. For each sample, the composition determined using $^1$H NMR spectroscopy (d$_7$-DMF) matched closely the theoretical composition. Moreover, the gravimetric yield was high (85-99%) in all cases which suggests that low molar mass polymers (which, if present, are expected to be higher in PMVL content), are not removed by fractionation during the precipitation step. The molar mass and dispersity were determined using SEC (DMF). Typical of step growth polymerization, a majority of the TPU samples were characterized by dispersity values close to 2.0. However, M3000B (0.44) exhibited a slightly higher dispersity ($Đ$=2.64) which may indicate a small amount of chain coupling during the first step of the synthesis. Although all the TPU samples are ostensibly linear, it is possible that side reactions may cause the formation of lightly branched structures.

Generally, TPUs are segmented block polymers consisting of polyol soft segments connected by hard segments. Because they are prepared via random coupling, the hard segments (alternating copolymers of a diisocyante and diol chain extender) are of ill-defined length. Provided the molar masses of the individual segments are high enough, TPUs tend to phase separate to form a physically crosslinked material. All of the PMVL TPU samples exhibited a soft segment glass transition temperature (−50° C.≤$T_g$≤−30° C.) slightly elevated relative to PMVL homopolymer. This suggests partial inclusion of hard segment copolymer in the soft domains. The $T_g$ values tend to decrease with hard segment content, indicating better phase separation at these compositions. The PMVL TPUs displayed a broad endotherm near 200° C. (160° C.≤$T_m$≤220° C.). This may be due to strong hydrogen bonding in these materials. Fourier transform infrared spectroscopy (ATR-FTIR) provided further evidence of microphase separation. In addition to the characteristic ester carbonyl stretch (C=O, 1727 cm$^{-1}$) of PMVL, hydrogen bonded urethane stretches (C=O 1702 cm$^{-1}$ and C—N 1614 cm$^{-1}$) were observed. The position and intensity of the urethane N—H stretch (N—H 3324 cm$^{-1}$) is also a good indication of hydrogen bonding in these materials.

TABLE 1

Polyol Characteristics

| Sample ID | [a]Initiator | [b]$M_{n\ Theor.}$ (kg mol$^{-1}$) | [c]$M_{n,\ NMR}$ (kg mol$^{-1}$) | [d]$M_{n,\ MALDI}$ (kg mol$^{-1}$) | [d]$Đ_{MALDI}$ | [e]Yield (%) | $T_g$ (° C.) | [g]η (cP) |
|---|---|---|---|---|---|---|---|---|
| PMVL3000 | BDM | 2.6 | 3.0 | 2.4 | 1.19 | 89 | −63 | — |
| PMVL2900 | PD | 3.1 | 2.9 | 4.1 | 1.09 | 90 | −62 | — |
| PMVL5200 | BD | 5.6 | 5.2 | 5.0 | 1.54 | 99 | −60 | 4406 |
| PMVL2700 | TMP-EO | 2.8 | 2.7 | 3.4 | 1.07 | 95 | −62 | 1643 |

[a]The indicated diol initiators are 1,4 benzene dimethanol (BDM), 1,3 propane diol (PD), and 1,4 butane diol (BD). The triol initiator was an ethylene oxide functionalized trimethylolpropane (TMP-EO) with a nominal molar mass of ~170 g/mol. Based on MALDI analysis of the PMVL 2700 triol (FIG. 2b), the initiating species with 0, 1, 2, and 3 EO repeat units were deduced to all be present.
[b]The theoretical molar mass calculated from molar ratio of MVL:Initiator and monomer conversion as determined by $^1$H NMR.
[c]Molar mass estimated by $^1$H NMR end group analysis.
[d]Molar mass and dispersity determined by MALDI; these values are compared to those found using SEC in the SI.
[e]Gravimetric yield of recovered polyol based on observed monomer conversion.
[g]Zero shear viscosity at 25° C.

TABLE 2

Characteristics of TPUs from PMVL

| [a]Sample ID | [b]$M_n$ (kg mol$^{-1}$) | [b]$D$ | [c]$T_g$ (° C.) | [c]$T_m$ (° C.) | [c]$\Delta H$ (J g$^{-1}$) | [e]Yield (%) | [f]$\sigma_b$ (MPa) | [f]$\varepsilon_b$ (%) | [f]$E_y$ (MPa) |
|---|---|---|---|---|---|---|---|---|---|
| M2900P(0.40) | 102.2 | 1.63 | −33 | 202 | 12.8 | 87 | 37 ± 3 | 1000 ± 20 | 7.2 ± 0.2 |
| M2900P(0.41) | 31.8 | 1.98 | −33 | 162 | 7.03 | 87 | 6.4 ± 0.2 | 285 ± 30 | 4.3 ± 0.2 |
| M3000B(0.44) | 49.9 | 2.64 | −35 | 192 | 13.5 | 89 | 6.4 ± 0.2 | 250 ± 50 | 2.6 ± 0.1 |
| M3000B(0.53) | 30.5 | 1.46 | −47 | 196 | 19.2 | 93 | 9.3 ± 0.2 | 72 ± 7 | 46 ± 2 |
| M3000B(0.60) | 40.3 | 2.02 | [d]na | 221 | 27.8 | 86 | 19.4 ± 0.6 | 82 ± 15 | 116 ± 3 |

[a]The sample name is composed of three parts where (M####) indicates the molar mass of the PMVL diol precursor in g mol$^{-1}$, the letter P or B indicates the chain extender used (propane diol or butane diol, respectively), and the parenthetical numbers indicate the hard segment content (determined using $^1$H NMR spectroscopy). More specifically, % HS = 100*(MDI + CE)/(MDI + CE + PMVL) where MDI, CE, and PMVL are, respectively, the isocyanate, chain extender, and polyol components.
[b]Relative molar mass and dispersity were determined by SEC (DMF, PS standards).
[c]Determined using DSC, taken on the second heating ramp at a rate of 10° C. min$^{-1}$.
[d]Not observed by DSC on the second heating ramp; by DMA this sample has a $T_g$ of −50° C.
[e]Gravimetric yield of the purified TPU.
[f]Ultimate tensile strength ($\sigma_b$) and maximum elongation ($\varepsilon_b$) are the stress and elongation at break. Elastic modulus ($E_y$), $\sigma_b$, and $\varepsilon_b$, were determined using uniaxial extension tests at a constant crosshead velocity of 60 mm min$^{-1}$.

Figure 5A:
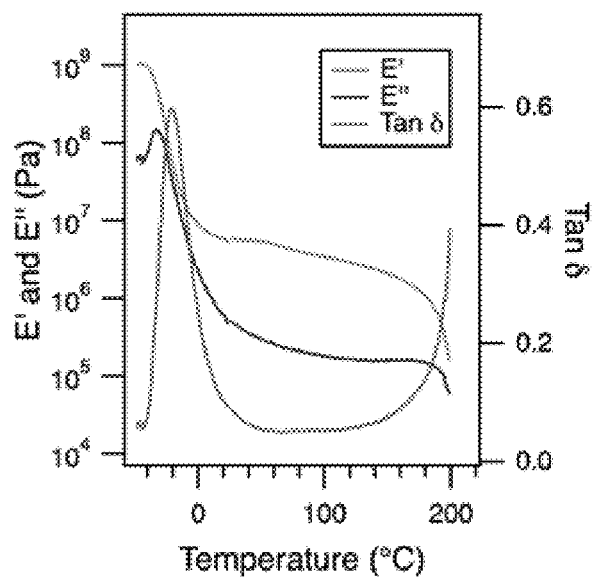
FIG. 5A is plot of dynamic mechanical analysis (DMA) of PMVL TPU M2900P (0.40). Data was taken in tension film mode at a heating rate of 3° C. min$^{-1}$ and a frequency of 1 Hz.

Dynamic mechanical analysis (DMA) was used to corroborate the IR and DSC results. Compression molded rectangular strips were tested in tension mode. The samples were cooled through the glass transition, and then heated until the material began to flow ($T_f$), as indicated by rapid decrease in modulus. This is shown with PMVL TPU M2900P as an example in FIG. 5A. For each sample, the glass transition determined by DMA was similar to values found using DSC. The gently sloping plateau in E' and E" (for $T_g \leq T \leq T_f$) is another good indication that the TPUs are microphase-separated. Although the softening of the material at high temperatures could be interpreted as degradation, follow-up DMA experiments (operating in shear mode) found that this transition was reversible on cooling. This was interpreted as restoration of hydrogen bonded segments in the material.

Figure 5B:
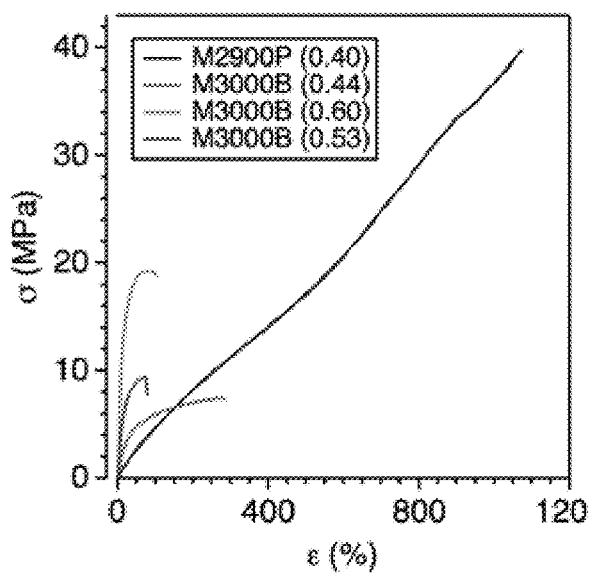
FIG. 5B is a plot of representative tensile data obtained for uniaxial extension of PMVL TPUs. Experiments were conducted with a constant crosshead velocity of 60 mm min$^{-1}$.

Mechanical properties of the TPUs, studied by uniaxial extension tests, were dependent on the molecular structure of the polymer (see FIG. 5B for representative examples). For a series of polymers with similar overall molar mass, i.e., M3000B (0.44), (0.53), and (0.60), the elastic modulus and stress at break both increased with hard segment content. When the composition was fixed, tensile properties depend on the overall molar mass. Despite similar composition, sample M2900P (0.40), for example, had a stress at break that was nearly six times larger than M2900P (0.41), an analogous sample of lower overall molar mass. Due to their high hard segment content, the majority of the PMVL TPU samples exhibited mechanical performance more typical of tough plastics than elastomers. However M2900P (0.40) demonstrated excellent elasticity during hysteresis testing, with nearly complete recovery of applied strain over 20 cycles. This sample in particular is mechanically comparable to soft commercial thermoplastic polyurethanes.

The characteristics of a few representative foams are summarized in Table 3. Similar to the TPUs described above, the foam samples may be idealized as segmented block polymers consisting of PMVL soft segments connected by hard segments rich in urethane or urea linkages. In the foam formulations used herein, water reacts with the isocyanate groups of TDI to form an unstable carbamic acid that subsequently decomposes to generate $CO_2$ (blowing reaction) and a primary amine. The PMVL polyol and aromatic amines react simultaneously with TDI to create a crosslinked network (gelling reaction). The nanoscopic phase behavior of the resulting polyurethane is largely determined by the size and functionality of the polyol segment, the relative rates of the blowing and gelling reactions, and the ratio of TDI to polyol and water. The microscopic structure of the foam is influenced by both phase behavior of the polyurethane and the ability of the surfactant to stabilize the polymer foam as it rises.

TABLE 3

*Characteristics of PMVL Foams

| [a]Sample ID | [b]TDI (wt %) | [c]$T_g$ (° C.) | [c]$T_g$ (° C.) | [d]$\rho$ (kg m$^{-3}$) | [e]$\sigma_T$ (kPa) | [f]$\varepsilon_b$ (%) | [g]$\sigma_{(C50)}$ (kPa) | [h]K (kPa) |
|---|---|---|---|---|---|---|---|---|
| M2700-A | 26 | −33 | 132 | 40 ± 3 | 210 ± 30 | 250 ± 70 | 4.3 ± 0.2 | 3.0 ± 0.5 |
| M2700-B | 24 | −38 | 130 | 47 ± 9 | 160 ± 20 | 350 ± 60 | 4.8 ± 0.7 | 3.0 ± 0.4 |
| M2700-C | 21 | −37 | 126 | 80 ± 10 | 390 ± 80 | 130 ± 20 | 8.3 ± 0.6 | 3.3 ± 0.5 |
| M2700/5200-D | 14 | −39 | 128 | 47 ± 5 | 130 ± 25 | 570 ± 140 | 3.3 ± 0.3 | 1.0 ± 0.1 |

*Density and mechanical characteristics of foams are reported as the average and standard deviation of a minimum of five samples. Extension and compression tests were conducted parallel to the direction of the foam rise.
[a]Sample ID refers to the polyol used in the foam formulation.
[b]TDI content (wt %) in the foam formulation. For these particular samples, the masses of all other components (catalysts, PMVL, water, and surfactant) were fixed. The full formulation for each sample is specified in the SI.
[c]Glass transition temperatures were measured using DSC and were taken on the second heating at a ramp rate of 10° C. min$^{-1}$.
[d]Density reported is the mass of a small cube cut from the core of a foam sample and divided by its measured volume. The top and bottom sections of the foam were not tested due to difference in appearance and density.
[e]Ultimate tensile strength is defined as the stress at failure.
[f]Maximum elongation is designated as strain at failure.
[g]Compressive strength is defined as stress at 50% compression.
[h]Compressive modulus ($\sigma/\varepsilon$) over the linear regime.

Figure 6A:
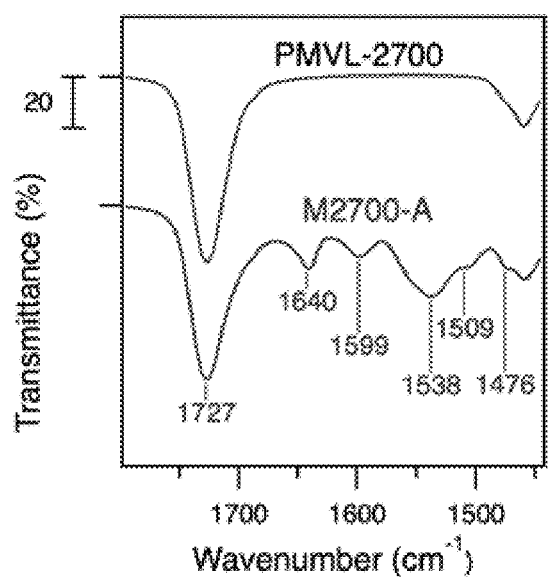
FIG. 6A is an attenuated total reflectance (ATR)-Fourier transform infrared (FTIR) spectroscopy plot of PMVL2700 triol and PMVL polyurethane (PU) foam M2700-A. The spectra have been shifted vertically for clarity and ticks on the y-axis represent 100% transmittance for the respective samples.
Figure 6B:
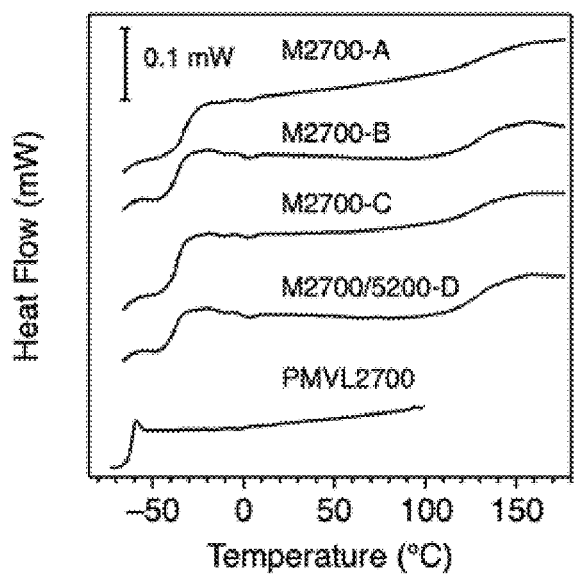
FIG. 6B depicts a differential scanning calorimetry (DSC) thermograms of PMVL triol and PMVL PU foams. To avoid degradation, the PMVL triol was not heated above 100° C.

ATR-FTIR spectroscopy was used to provide insight on the molecular structure and composition of the crosslinked PMVL PU foams. All of the IR signals of PMVL homopolymer are preserved in the spectrum of the foam. As shown in FIG. 6A, the characteristic PMVL ester carbonyl stretch (C=O, 1727 cm$^{-1}$) largely obscures the region where urethane or free urea cabonyl stretches are expected to occur. However, an additional signal, which likely corresponds to the stretch of hydrogen bonded urea carbonyls (C=O, 1640 cm$^{-1}$), is observed. Broad signals, attributable to the N—H stretches of hydrogen bonding monodentate and bidentate ureas, are also present (at 3400-3245 cm$^{-1}$), as are characteristic N—H bends (near 1540 cm$^{-1}$). Of these, the stretch at 1640 cm$^{-1}$ is a characteristic feature of organized hard domains, implying a microphase-separated structure. Further evidence of a segregated structure was found using DSC (FIG. 6B). Each of the PMVL foams exhibit two $T_g$ values, one near −35° C., the other near 130° C. The lower $T_g$ value is in every case higher than that of the polyol precursor (−60° C.), an observation that suggests partial mixing of the soft and hard domains. Within the temperature range of the DSC experiment (−80° C.<T<180° C.) the sample was amorphous; however, that bidentate urea hydrogen bonds are unlikely to melt below the degradation temperature of the material.

Foam properties and cellular structure were tuned by changing both the TDI content in the formulation and the PMVL polyol. Samples M2700-A, M2700-B, and M2700-C in Table 3 were prepared using the same PMVL triol (2.7 kg mol$^{-1}$ with a nominal functionality of 3.0) but differ in the amount of TDI. Although the compressive modulus for A and B are similar, the compressive strength (defined in this work as the stress at 50% compression) is much higher for sample C. M2700/5200-D was prepared from a blend of PMVL2700 triol and PMVL5200 diol, and displayed the lowest compressive strength and modulus of the PMVL foams. For all four samples there is an inverse correlation between elongation at break and ultimate tensile strength. The lab scale tests were used to characterize the mechanical properties of the foams were not ASTM standard (due to small sample size and equipment limitations), therefore it may not be possible to directly compare to the published values for soft flexible foams. However, the mechanical properties of a series of commercial flexible polyurethane foams of different firmness grades (McMaster-Carr Foams MCM00111, MCM00131, MCM00017) were analyzed using the same tensile and compression testing procedures. The PMVL foams were found to have similar compression modulus and compression strength to soft commercial foams but exhibit improved tensile strength and elongation.

Figure 7A:
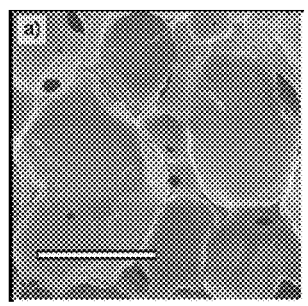
FIGS. 7A-F are scanning electron micrograph (SEM) images of PMVL PU foams of different compositions. In all images the white bar represents 1 mm.
Figure 7B:
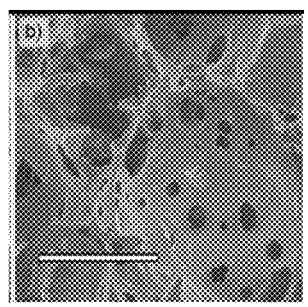
Figure 7C:
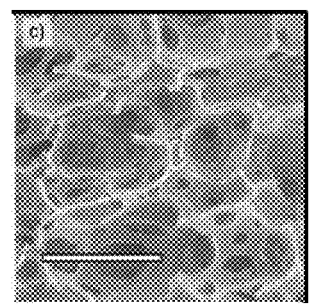
Figure 7D:
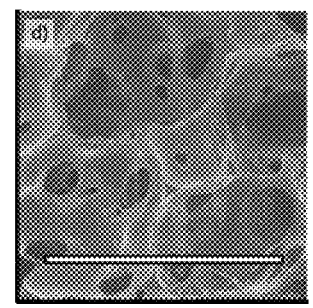
Figure 7E:
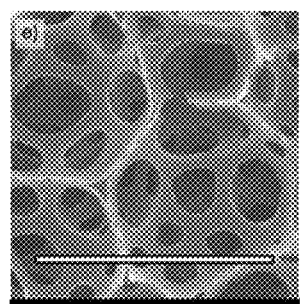
Figure 7F:
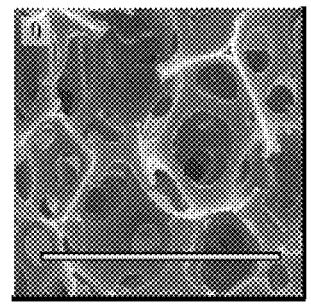

PMVL foam samples A, B, and D exhibit densities similar to commercial polyether based slab-stock foams made using water and commercial grade TDI (most typically, 12-60 kg m$^{-3}$). However, the density of foam sample C is nearly twice that of the other foams. The primary difference between these foams is their cell structures (FIGS. 7A-D). Foams samples A and B, prepared with similar TDI content, both exhibited large closed cells of irregular size. Samples C and D, prepared using less TDI, exhibited much smaller cell sizes. Sample C is primarily open cell with more geometric structures and relatively thick struts. In contrast, Sample D consisted of more rounded cells that were partially opened. An analogous foam with similar TDI content prepared using only PMVL2700 triol produced a fully open cell, suggesting that inclusion of the higher viscosity PMVL diol may also impact the cell structure significantly (FIG. 7E).

The thermal stability of both foam and elastomer samples was analyzed using thermogravimetric analysis (TGA). For these studies, the degradation temperature ($T_d$) is defined as the temperature at which 5% mass loss is observed on heating under nitrogen at a ramp rate of 10° C. min$^{-1}$. Compared to PMVL homopolymer ($T_d$=150° C.) elastomers ($T_d$=225-245° C.) and foams ($T_d$=220-250° C.) both exhibit improved temperature stability compared to PMVL homopolymer. For both types of polyurethane, the degradation temperature increased slightly with the isocyanate.

Figure 8A:
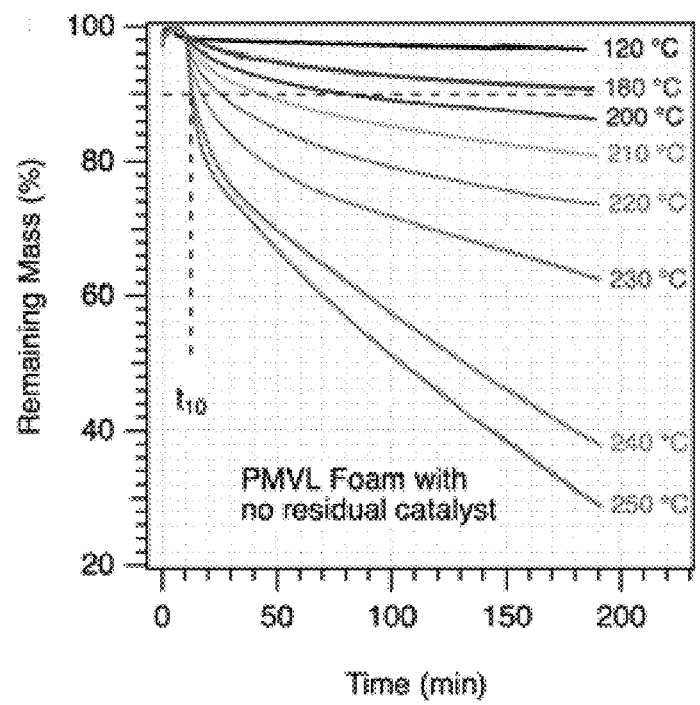
FIG. 8A is an overlay showing mass loss of M2700-A foam during isothermal annealing at indicated temperatures. Similar data are shown for PMVL TPUs, PMVL homopolymer, and PMVL foam with Sn(Oct)$_2$ catalyst. The dashed lines define $t_{10}$, the time at a specific temperature (shown for 225° C.) at which 10% of the starting mass is lost.
Figure 8B:
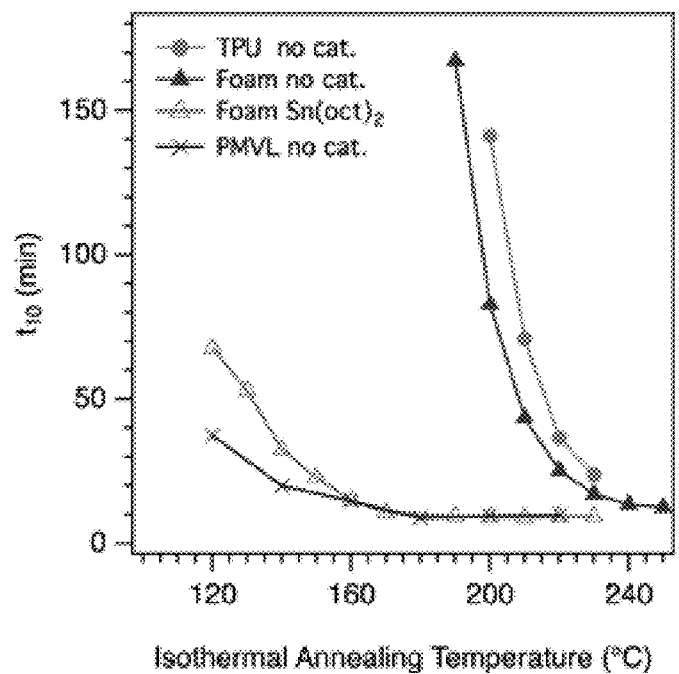
FIG. 8B is a plot showing the dependence of $t_{10}$ for (-●-) M2900P (0.40) TPU precipitated to remove catalyst, (-▲-) *M2700-A PU foam prepared using only amine catalysts, (-Δ-) PMVL foam of same composition prepared using both amine catalysts and Sn(Oct)$_2$, and (-X-) PMVL2700 triol precipitated to remove catalyst. *Amine catalysts are believed to still be contained within the foam sample and are volatilized and removed from the foam upon heating.

Isothermal annealing experiments were conducted to examine the stability of PMVL polyurethanes over time. If no catalyst was present, both foam and elastomer samples were stable when annealed at temperatures below 180° C.; however mass loss was significantly accelerated at higher temperatures (FIG. 8A). As a specific example, TPU sample M2900P (0.40) exhibits only 3% mass loss after 4 h at 180° C. but 18% mass loss after 4 h at 200° C. The annealing time required for 10% mass loss at a specific temperature ($t_{10}$) was used to directly compare the stability of different samples (summarized in FIG. 8B). Foam samples prepared using organocatalysts exhibit similar stability to TPU samples without residual catalyst (removed by precipitation). However, degradation is significantly faster for samples prepared using a tin catalyst (Sn(Oct)$_2$). These results are rather dramatic but are in good agreement with previous studies regarding the impact of residual catalysts on the degradation of aliphatic polyesters.

To recycle PMVL foams back into MVL monomer, the thermodynamic tendency of PMVL was exploited to depolymerize at elevated temperatures by simply heating neat foam samples in a short path distillation apparatus under dynamic vacuum (200-250° C., ~100 mTorr). During the recycling process all volatile products were collected in a receiving flask cooled by liquid nitrogen. It is possible to recycle foams prepared using only amine catalysts; however, the recycling reaction was found to be faster when Sn(Oct)$_2$ was present (either added during the foam formulation or to the foam immediately prior to recycling). Although the MVL yield (50 to 99%) was dependent on temperature, foam composition, and catalyst concentration, in all cases the monomer was isolated in high purity (≥95% by $^1$H NMR spectroscopy). Since MVL monomer may be continuously removed by distillation, it is also possible to recycle MVL foams mixed with foams derived from other polyols. To demonstrate this, PMVL foam was mixed with an equal mass of commercial polyurethane foam and conducted a recycling experiment under the same conditions used to recycle pure PMVL foams (200-250° C., ~100 mTorr). In this mixed recycling experiment no significant decrease in the recovery or purity of MVL was observed.

Figure 9A:
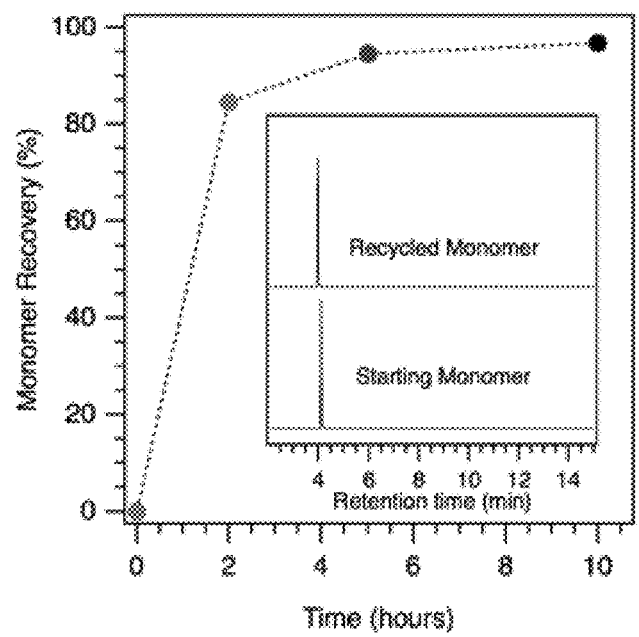
FIG. 9A is a plot showing MVL recovery over time during a 10 hour distillation experiment conducted at 225° C. Overlay shows GC chromatographs of recovered monomer (cumulative after 10 hours) compared to the pure MVL originally used to prepare the PMVL polyol contained in the foam (inset).
Figure 9B:
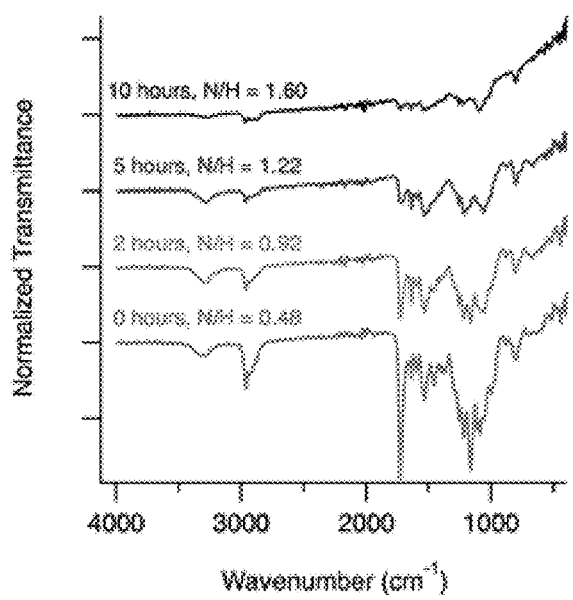
FIG. 9B is an ATR-FTIR plot of foam residue from distillation flask at indicated time. The N/H mass ratio, determined by elemental analysis (average of two samples), is also indicated for each.

The monomer recovery of MVL from PMVL foam over time was also measured. FIG. 9A shows that 85% of MVL monomer was recovered within the first two hours of distillation at 225° C. Longer reaction times resulted in slightly higher yields (a total yield of 97% after ten hours), but monomer recovery was slower during the final stages of the process. In a parallel experiment, samples of degraded foam and aliquots of recovered monomer were removed from the distillation after two, five, and ten hours. Over the course of the distillation there was no significant change in the purity of the recovered MVL; all of the samples analyzed were greater than 99% pure by gas chromatography (GC). The samples of foam residue were insoluble; however, elemental analysis revealed an increase in nitrogen content. The FTIRs of the degraded foam samples (FIG. 9B), displayed a concomitant decrease in the intensity of stretch corresponding to the PMVL ester (1729 cm$^{-1}$) carbonyl. Taken together, the IR and elemental analysis results are consistent with removal of MVL and retention of cross-linked urea and high boiling amine products.

To demonstrate the utility of this recycling approach, MVL recovered from the depolymerization of PMVL foam was used to prepare new PMVL polyols. An alcohol initiator (1,4 butane diol) and an acid catalyst (HCl in ether) were added directly to the receiving flask containing MVL from the distillation experiment. The flask was capped and the contents stirred until the reaction reached equilibrium, followed by removal of the catalyst under vacuum. The molar mass of the resulting PMVL ($M_{n,\ MALDI}$=2.08 kg mol$^{-1}$, Đ=1.55) was close to the theoretical molar mass ($M_{n,\ theor.}$=2.28 kg mol$^{-1}$). In this sample, the majority of PMVL were initiated by 1,4 butane diol; however some chains were initiated by very minor contaminants, e.g., diaminotoluene. These contaminants were higher boiling and could be removed by fractional distillation. Thus, recycled MVL purified in this manner could be used to prepare a new polyol that is, by MALDI, indistinguishable from an analogous sample prepared from virgin monomer.

Discussion

The ease and versatility of synthesis makes PMVL polyols attractive alternatives to biobased polyols for a variety of applications. Because MVL is polymerized in the bulk at room temperature without the use high temperatures or solvents, the synthesis of PMVL polyols fully embodies the tenets of green chemistry. The use of HCl as a ROTEP catalyst is convenient for the synthesis of low molar mass polyols as it may be removed under reduced pressure, avoiding the precipitation step previously required to remove catalyst and unreacted monomer. Precise control over the ring opening polymerization of MVL enables the synthesis of PMVL polyols with tailored functionality and molar masses. Whereas NOPs typically have complex molecular structures due to the heterogeneous triglyceride mixtures present in plant oil, PMVL polyols are well defined. In this regard, biobased PMVL is more similar to petrochemical polyetherols than natural oil polyols.

In the past, a variety of other lactones have been explored as starting materials for the synthesis of polyesterol polyurethanes. Poly(ε-caprolactone) (PCL) derived TPUs, for example, have been explored for use in degradable medical devices. Neat PCL, however, is semicrystalline ($T_m$=60° C.) and is an unsuitable building block for applications where high elasticity is required. Alkyl-substituted aliphatic polyesters, such as the renewable polymers poly(δ-decalactone) and poly(carvomenthide), are amorphous and may be used to prepare polyurethanes, but the precursor monomers are much more expensive than MVL. Additionally, these telechelic polymers are secondary alcohols, making them less reactive than PMVL.

Because PMVL is easily synthesized, reactive, bioderived, and potentially low-cost, it is an appealing building block for the manufacture of sustainable commodity materials. To demonstrate this, PMVL was shown to be successfully integrated into products that require distinct polyol characteristics, namely TPUs and PU foams. In general, TPUs prepared from natural oils may be somewhat soft, due to the presence of long dangling alkyl chains that may act as plasticizers. Commercial polyurethanes, however, are most typically prepared from polyesters or polyethers without long dangling branches. The methyl-substituents of PMVL are sufficient to render the soft segments amorphous but do not inhibit hydrogen bonding between the ester and urethane segments. Consequently, use of PMVL as a soft segment enables the synthesis of TPUs with excellent mechanical properties, similar to soft commercial TPUs (most typically these materials exhibit a strain at break of 350-800% and a stress at break of 20-50 MPa).

Soft segment dangling ends may also contribute to inferior properties in PU foams. To combat this problem, and to increase reactivity, vegetable oil polyols are typically mixed with petroleum-based polyols when used to prepare polyurethanes. In foams, this blending strategy limits total bioderived content but generally results in better density control, more homogeneous cell structures, and better mechanical performance. In this work, foams using PMVL as the sole polyol were prepared, leading to materials with high bioderived content. Using a two-component, one-pot procedure, PMVL foams were produced with compression properties and densities similar to commercial soft foams. The properties of the foam were able to be adjusted by changing the ratio of isocyante:PMVL in the formulation. Although the biodegradability of the PMVL TPUs or foams were not investigated, polyurethanes with structurally similar soft segments have previously been shown to be susceptible to hydrolysis by microbial esterase enzymes. It is therefore believed that these bioderived materials are also biodegradable, adding to their attractiveness as new sustainable materials.

As noted previously, the thermal stability of the PMVL materials studied in this work depend on a number of factors. PMVL polyol has low thermal stability due to its thermodynamic tendency to depolymerize when heated. This presumably occurs via unzipping depolymerization off the end polymer and is faster for low molar mass polymers, due to a higher concentration of hydroxyl end groups. The thermal stability of the PMVL TPUs (provided no residual catalyst is present) is improved because the hydroxyl end groups of the polymer have reacted with isocyanates and are no longer available to participate in depolymerization or transesterification reactions. Blocking the end group of the polymer with a urethane cannot fully prevent thermal degradation from occurring. Water molecules—either adsorbed on the surface of the polymer or generated by decarboxylation of other degradation products—may hydrolyze the PMVL backbone in situ leading to the formation of new alcohol endgroups.

Additionally, the urethane bond is reversible; in a pyrolytic environment it may reverse on heating to form isocyanates and alcohols (typically at 180° C.≤$T_d$≤250° C.). It is believed that this dissociation mechanism, and subsequent depolymerization of the resulting hydroxy-terminated PMVL, is the major degradation pathway for PMVL PUs under pyrolysis conditions. Consistent with this interpretation, when no catalyst is present both types of PMVL PUs (foams and thermoplastics) are stable at temperatures below the expected reversion temperature of the urethane bond. Practically, information about PMVL TPU stability may be used in conjunction with DMTA data to help define the appropriate use and processing conditions for a given sample. Although the foams are chemically cross-linked and cannot be thermally processed, knowledge of the thermal stability may also be used to help design the optimal conditions for chemical recycling.

As discussed previously, one of the major factors that precludes chemical recycling of polyurethane foams is limited purity of the recovered polyol. Glycolysis and hydrolysis, two potential chemical PU recycling methods, suffer from heterogeneity in the recovered polyol itself (i.e., range of functionality and molar mass) and non-polyol contaminants from potential side reactions. This is further complicated in the presence of mixed waste streams when the recovered polyol may consist of a variety of polymer types (e.g., polyesters and polyethers). Ultimately, these recycled polyols cannot be incorporated into high-value products, as concerns over quality control arise due to batch-to-batch variation.

Figure 10:
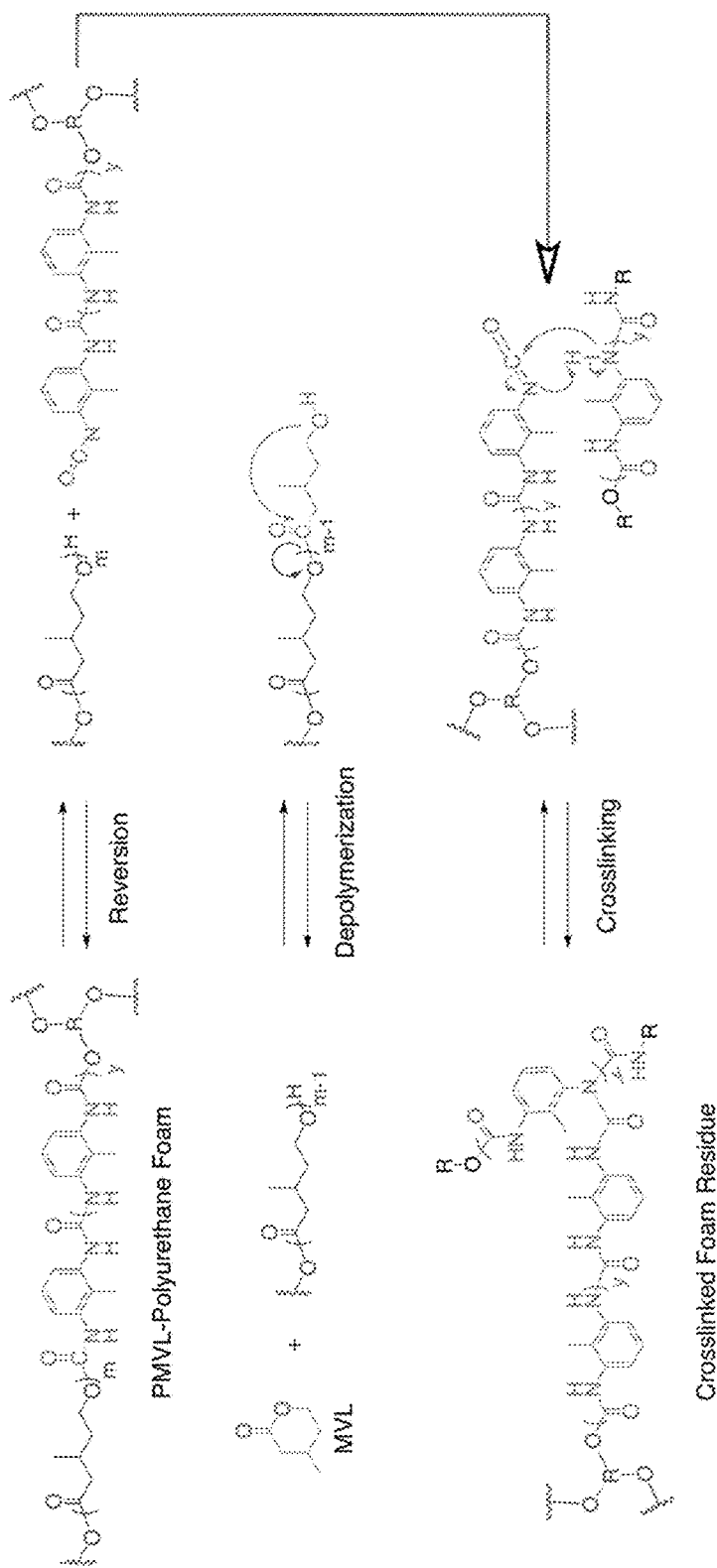
FIG. 10 is a reaction scheme illustrating an embodiment for recycling PMVL foams to recover MVL. In the first step PMVL polyurethane foam degrades by reversion of the polyurethane bond to form PMVL-OH and a crosslinked isocyanate-terminated polymer. The PMVL quickly depolymerizes to yield MVL monomer, which is continuously removed by distillation. The isocyanate reacts with urethane or urea linkages in the remaining foam to for respectively, allophanate or biuret linkages.

The recycling method described for PMVL-derived materials removes concerns over polyol heterogeneity because it directly regenerates the original MVL monomer, bypassing recovery of the polyol entirely (FIG. 10). Thus, because monomer is recovered in high yield and purity, it may be polymerized into PMVL with precisely targeted functionality and molar mass. This, in turn, may be used in a variety of PU applications, including new foams and elastomers, with the same integrity as the originally synthesized PVML polyol. This method truly embodies a cyclic lifecycle with little waste and low energy cost, resulting in an overall value-added approach.

The pyrolytic recycling method takes advantage of the polyurethane reversion and the thermodynamic tendency of PMVL to depolymerized at elevated temperatures, demonstrated in FIG. 10. Although it is possible to recycle foams using only amine catalysts as the blowing and gelling catalysts, the rate of PMVL depolymerization may be accelerated by the addition of $Sn(Oct)_2$. This catalyst is often used as a gelling catalyst in industrial flexible PU foam formulations, so its incorporation into a PMVL-derived foam formulation would benefit both production and recycling. Running the distillation at 225° C. under vacuum with $Sn(Oct)_2$ present at 0.14%, 85% recovery of MVL monomer after only 2 hours, and upwards of 96% after ten hours, was shown.

The relatively low MVL boiling point (BP) enables monomer recovery at high purity under the described conditions (BP~35° C. at 0.1 Torr). It is assumed that diaminotoluene isomers (BP~69° C. at 0.1 Torr), which could conceivably be formed from the degradation of urea bonds, do not accumulate in appreciable amounts, as they are not observed in the GC chromatograph or the $^1H$ NMR spectrum of the recovered material. Likely, any isocyanate-terminated polymers formed in situ by reversion of the urethane bond quickly react with urea or urethane functionalities in the foam; forming a highly crosslinked material. When considering the crosslinked foam residue that remains after the distillation, in theory, it should also be possible to recover additional foam reagents such as initiator polyols (e.g., trimethylolpropane) and amines using split phase glycolysis. This would further increase the attractiveness of PMVL PU materials from a waste reduction standpoint.

Conclusions

The potential of renewable lactone MVL as a versatile building block for the synthesis of functional materials has been investigated. Analogous to commercial polyether polyols, PMVL may be synthesized with a high degree of synthetic control. Unlike many bioderived polyols, the molecular weight and functionality of PMVL may be easily tuned to access polyols for a wide range of applications. This was briefly demonstrated using a divergent approach. In one example, PMVL diols of various molar masses were reacted with MDI and an alcohol chain extender to prepare thermoplastic polyurethanes. In a second example, a PMVL triol was reacted with TDI and water to prepare flexible foams. In both cases, the properties of the resulting materials may be tuned in a predictable manner by adjusting synthetic parameters (e.g. polyol molar mass and ratios of isocyanate:chain extender:polyol). Encouragingly, both the foam and TPU materials compared favorably to commercial analogs. Excitingly, that PMVL polyurethanes may be recycled back to MVL monomer in high purity and yield using a simple pyrolysis approach has been demonstrated. Because the moderate boiling point of the lactone facilitates its removal and separation from other degradation products, this strategy bypasses many of the technical challenges that currently preclude chemical recycling of polyurethanes on an industrial scale.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, the term "about" encompasses the range of experimental error that occurs in any measurement.

Thus, embodiments of RECOVERY OF MONOMER FROM POLYURETHANE MATERIALS BY DEPOLYMERIZATION are disclosed. One skilled in the art will appreciate that the compounds, compositions, polymers and methods described herein can be practiced with embodiments other than those disclosed. The disclosed embodiments are presented for purposes of illustration and not limitation. One will also understand that components, embodiments, or aspects of the compounds, compositions, polymers, and methods described herein may be interchangeable as appropriate.

What is claimed is:

1. A method for recovering a lactone monomer from a polymer comprising polyester derived from lactone monomer, wherein the lactone has a bulk ceiling temperature of 600° C. or less, the method comprising:

heating the polymer to cause depolymerization and release of the lactone monomer from the polyester; and recovering the released lactone monomer, wherein the polyester has a glass transition temperature of 20° C. or less.

2. A method according to claim 1, wherein the lactone monomer is selected from the group consisting of an alkyl-substituted δ-lactone and ε-caprolactone and a γ-lactone monomer.

3. A method according to claim 1, wherein the lactone monomer is selected from the group consisting of δ-decalactone, α-methyl-δ-valerolactone, and γ-methyl-δ-valerolactone.

4. A method according to claim 1, wherein the polymer is a thermoset polyurethane.

5. A method according to claim 1, wherein the polymer is a block copolymer comprising a polyester block.

6. A method for recovering a monomer from a polymer comprising homopolymer block, wherein the homopolymer block has a bulk ceiling temperature of 600° C. or less, the method comprising:

heating the polymer to cause depolymerization and release of the monomer; and recovering the released monomer.

7. A method according to claim 6, wherein the homopolymer block has a glass transition temperature of 20° C. or less.

\* \* \* \* \*